(12) United States Patent
Blum et al.

(10) Patent No.: US 7,926,940 B2
(45) Date of Patent: Apr. 19, 2011

(54) ADVANCED ELECTRO-ACTIVE OPTIC DEVICE

(75) Inventors: Ronald D. Blum, Roanoke, VA (US); Joshua N. Haddock, Roanoke, VA (US); William Kokonaski, Gig Harbor, WA (US); Amitava Gupta, Roanoke, VA (US)

(73) Assignee: PixelOptics, Inc., Roanoke, VA (US)

( * ) Notice: Subject to any disclaimer, the term of this patent is extended or adjusted under 35 U.S.C. 154(b) by 0 days.

(21) Appl. No.: 12/406,656

(22) Filed: Mar. 18, 2009

(65) Prior Publication Data

US 2009/0204207 A1    Aug. 13, 2009

Related U.S. Application Data

(63) Continuation-in-part of application No. 12/035,779, filed on Feb. 22, 2008.

(60) Provisional application No. 60/902,866, filed on Feb. 23, 2007, provisional application No. 61/020,759, filed on Jan. 14, 2008, provisional application No. 61/025,348, filed on Feb. 1, 2008, provisional application No. 61/029,469, filed on Feb. 18, 2008, provisional application No. 61/037,351, filed on Mar. 18, 2008, provisional application No. 61/060,291, filed on Jun. 10, 2008.

(51) Int. Cl.
*G02C 7/10* (2006.01)
(52) U.S. Cl. ........................................ 351/163; 351/165
(58) Field of Classification Search ........... 351/159–176
See application file for complete search history.

(56) References Cited

U.S. PATENT DOCUMENTS

| | | | |
|---|---|---|---|
| 2,437,642 A | 3/1948 | Henroleau |
| 2,576,581 A | 11/1951 | Edwards |
| 3,161,718 A | 12/1964 | De Luca |
| 3,245,315 A | 4/1966 | Marks et al. |
| 3,248,460 A | 4/1966 | Naujokas |
| 3,309,162 A | 3/1967 | Kosanke et al. |
| 3,614,215 A | 10/1971 | Mackta |
| 3,738,734 A | 6/1973 | Tait et al. |
| 3,791,719 A | 2/1974 | Kratzer et al. |
| 4,062,629 A | 12/1977 | Winthrop |
| 4,174,156 A | 11/1979 | Glorieux |
| 4,181,408 A | 1/1980 | Senders |
| 4,190,330 A | 2/1980 | Berreman |
| 4,190,621 A | 2/1980 | Greshes |

(Continued)

FOREIGN PATENT DOCUMENTS

CN    ROC89113088    10/2001

(Continued)

OTHER PUBLICATIONS

Teng et al, Nanoparticles-doped guest-host liquid crystal displays, Aug. 1, 2008,Optics Letters, pp. 1663-1665.*

(Continued)

*Primary Examiner* — Darryl J Collins
(74) *Attorney, Agent, or Firm* — Kilpatrick Townsend and Stockton LLP

(57) ABSTRACT

Optical devices having a dynamic aperture and/or an apodization mask are provided. The aperture and/or mask may be provided by one or more electro-active elements, and may be used in an ophthalmic device that that is spaced apart from but in optical communication with an intraocular lens, a corneal inlay, a corneal onlay, or a spectacle lens that provide an optical power.

32 Claims, 22 Drawing Sheets

U.S. PATENT DOCUMENTS

| | | |
|---|---|---|
| 4,264,154 A | 4/1981 | Petersen |
| 4,279,474 A | 7/1981 | Belgorod |
| 4,300,818 A | 11/1981 | Schachar |
| 4,320,939 A | 3/1982 | Mueller |
| 4,373,218 A | 2/1983 | Schachar |
| 4,395,736 A | 7/1983 | Fraleux |
| 4,418,990 A | 12/1983 | Gerber |
| 4,423,929 A | 1/1984 | Gomi |
| 4,457,585 A | 7/1984 | DuCorday |
| 4,461,550 A | 7/1984 | Legendre |
| 4,466,703 A | 8/1984 | Nishimoto |
| 4,466,706 A | 8/1984 | Lamothe, II |
| 4,529,268 A | 7/1985 | Brown |
| 4,564,267 A | 1/1986 | Nishimoto |
| 4,572,616 A | 2/1986 | Kowel et al. |
| 4,577,928 A | 3/1986 | Brown |
| 4,601,545 A | 7/1986 | Kern |
| 4,609,824 A | 9/1986 | Munier et al. |
| 4,712,870 A | 12/1987 | Robinson et al. |
| 4,756,605 A | 7/1988 | Okada et al. |
| 4,772,094 A | 9/1988 | Sheiman |
| D298,250 S | 10/1988 | Kildall |
| 4,781,440 A * | 11/1988 | Toda ............................. 349/15 |
| 4,787,733 A | 11/1988 | Silva |
| 4,787,903 A | 11/1988 | Grendahl |
| 4,795,248 A | 1/1989 | Okada et al. |
| 4,813,777 A | 3/1989 | Rainville et al. |
| 4,818,095 A | 4/1989 | Takeuchi |
| 4,836,652 A | 6/1989 | Oishi et al. |
| 4,842,400 A | 6/1989 | Klein |
| 4,869,588 A | 9/1989 | Frieder et al. |
| 4,873,029 A | 10/1989 | Blum |
| 4,880,300 A | 11/1989 | Payner et al. |
| 4,890,903 A | 1/1990 | Treisman et al. |
| 4,904,063 A | 2/1990 | Okada et al. |
| 4,907,860 A | 3/1990 | Noble |
| 4,909,626 A | 3/1990 | Purvis et al. |
| 4,919,520 A | 4/1990 | Okada et al. |
| 4,921,728 A | 5/1990 | Takiguchi |
| 4,927,241 A | 5/1990 | Kuijk |
| 4,929,865 A | 5/1990 | Blum |
| 4,930,884 A | 6/1990 | Tichenor et al. |
| 4,944,584 A | 7/1990 | Maeda et al. |
| 4,945,242 A | 7/1990 | Berger et al. |
| 4,952,048 A | 8/1990 | Frieder et al. |
| 4,952,788 A | 8/1990 | Berger et al. |
| 4,955,712 A | 9/1990 | Barth et al. |
| 4,958,907 A | 9/1990 | Davis |
| 4,961,639 A | 10/1990 | Lazarus |
| 4,968,127 A | 11/1990 | Russell et al. |
| 4,981,342 A | 1/1991 | Fiala |
| 4,991,951 A | 2/1991 | Mizuno et al. |
| 5,015,086 A | 5/1991 | Okaue et al. |
| 5,030,882 A | 7/1991 | Solero |
| 5,050,981 A | 9/1991 | Roffman |
| 5,066,301 A | 11/1991 | Wiley |
| 5,067,795 A | 11/1991 | Senatore |
| 5,073,021 A | 12/1991 | Marron |
| 5,076,665 A | 12/1991 | Petersen |
| 5,089,023 A | 2/1992 | Swanson |
| 5,091,801 A | 2/1992 | Ebstein |
| 5,108,169 A | 4/1992 | Mandell |
| 5,114,628 A | 5/1992 | Hofer et al. |
| 5,130,856 A | 7/1992 | Tichenor et al. |
| 5,142,411 A | 8/1992 | Fiala |
| 5,147,585 A | 9/1992 | Blum |
| 5,150,234 A | 9/1992 | Takahashi et al. |
| 5,171,266 A | 12/1992 | Wiley et al. |
| 5,178,800 A | 1/1993 | Blum |
| 5,182,585 A | 1/1993 | Stoner |
| 5,184,156 A | 2/1993 | Black et al. |
| 5,200,859 A | 4/1993 | Payner et al. |
| 5,208,688 A | 5/1993 | Fergason et al. |
| 5,219,497 A | 6/1993 | Blum |
| 5,229,797 A | 7/1993 | Futhey et al. |
| 5,229,885 A | 7/1993 | Quaglia |
| 5,231,430 A | 7/1993 | Kohayakawa |
| 5,239,412 A | 8/1993 | Naka et al. |
| D342,063 S | 12/1993 | Howitt et al. |
| 5,305,028 A | 4/1994 | Okano |
| 5,306,926 A | 4/1994 | Yonemoto |
| 5,324,930 A | 6/1994 | Jech, Jr. |
| D350,342 S | 9/1994 | Sack |
| 5,352,886 A | 10/1994 | Kane |
| 5,359,444 A | 10/1994 | Piosenka et al. |
| 5,375,006 A | 12/1994 | Haas |
| 5,382,986 A | 1/1995 | Black et al. |
| 5,386,308 A | 1/1995 | Michel et al. |
| 5,411,537 A | 5/1995 | Munshi et al. |
| 5,424,927 A | 6/1995 | Schaller et al. |
| 5,440,357 A | 8/1995 | Quaglia |
| 5,443,506 A | 8/1995 | Garabet |
| 5,451,766 A | 9/1995 | Van Berkel |
| 5,488,439 A | 1/1996 | Weltmann |
| 5,512,371 A | 4/1996 | Gupta et al. |
| 5,522,323 A | 6/1996 | Richard |
| 5,552,841 A | 9/1996 | Gallorini et al. |
| 5,608,567 A | 3/1997 | Grupp |
| 5,615,588 A | 4/1997 | Gottschald |
| 5,653,751 A | 8/1997 | Samly et al. |
| 5,654,786 A | 8/1997 | Bylander |
| 5,668,620 A | 9/1997 | Kurtin et al. |
| 5,682,223 A | 10/1997 | Menezes et al. |
| 5,683,457 A | 11/1997 | Gupta et al. |
| RE35,691 E | 12/1997 | Theirl et al. |
| 5,702,819 A | 12/1997 | Gupta et al. |
| 5,712,721 A | 1/1998 | Large |
| 5,728,155 A | 3/1998 | Anello et al. |
| 5,739,959 A | 4/1998 | Quaglia |
| 5,757,458 A | 5/1998 | Miller et al. |
| 5,777,719 A | 7/1998 | Williams et al. |
| 5,815,233 A | 9/1998 | Morokawa et al. |
| 5,815,239 A | 9/1998 | Chapman et al. |
| 5,859,685 A | 1/1999 | Gupta et al. |
| 5,861,934 A | 1/1999 | Blum et al. |
| 5,861,936 A | 1/1999 | Sorensen |
| 5,877,876 A | 3/1999 | Birdwell |
| 5,900,720 A | 5/1999 | Kallman et al. |
| 5,905,561 A | 5/1999 | Lee et al. |
| 5,949,521 A | 9/1999 | Williams et al. |
| 5,953,098 A | 9/1999 | Lieberman et al. |
| 5,956,183 A | 9/1999 | Epstein et al. |
| 5,963,300 A | 10/1999 | Horwitz |
| 5,971,540 A | 10/1999 | Ofner |
| 5,980,037 A | 11/1999 | Conway |
| 5,999,328 A | 12/1999 | Kurtin et al. |
| 6,040,947 A | 3/2000 | Kurtin et al. |
| 6,050,687 A | 4/2000 | Bille et al. |
| 6,069,742 A | 5/2000 | Silver |
| 6,086,203 A | 7/2000 | Blum et al. |
| 6,086,204 A | 7/2000 | Magnante |
| 6,095,651 A | 8/2000 | Williams et al. |
| 6,099,117 A | 8/2000 | Gregory |
| 6,115,177 A | 9/2000 | Vossler |
| 6,139,148 A | 10/2000 | Menezes |
| 6,145,987 A | 11/2000 | Baude et al. |
| 6,188,525 B1 | 2/2001 | Silver |
| 6,191,881 B1 | 2/2001 | Tajima |
| 6,199,984 B1 | 3/2001 | Menezes |
| 6,199,986 B1 | 3/2001 | Williams et al. |
| 6,213,602 B1 | 4/2001 | Smarto |
| 6,270,220 B1 | 8/2001 | Keren |
| 6,271,915 B1 | 8/2001 | Frey et al. |
| 6,282,449 B1 | 8/2001 | Kamerling et al. |
| 6,299,311 B1 | 10/2001 | Williams et al. |
| 6,305,802 B1 | 10/2001 | Roffman et al. |
| 6,325,508 B1 | 12/2001 | Decreton et al. |
| 6,338,559 B1 | 1/2002 | Williams et al. |
| 6,350,031 B1 | 2/2002 | Lashkari et al. |
| 6,390,623 B1 | 5/2002 | Kokonaski et al. |
| 6,396,622 B1 | 5/2002 | Alden |
| 6,437,762 B1 | 8/2002 | Birdwell |
| 6,437,925 B1 | 8/2002 | Nishioka |
| 6,464,363 B1 | 10/2002 | Nishioka et al. |
| 6,491,394 B1 | 12/2002 | Blum et al. |
| 6,501,443 B1 | 12/2002 | McMahon |
| 6,554,425 B1 | 4/2003 | Roffman et al. |

| | | |
|---|---|---|
| 6,609,794 B2 | 8/2003 | Levine |
| 6,614,408 B1 | 9/2003 | Mann |
| 6,616,275 B1 | 9/2003 | Dick et al. |
| 6,616,279 B1 | 9/2003 | Davis et al. |
| 6,618,208 B1 | 9/2003 | Silver |
| 6,626,532 B1 | 9/2003 | Nishioka et al. |
| 6,631,001 B2 | 10/2003 | Kuiseko |
| 6,638,304 B2 | 10/2003 | Azar |
| 6,643,552 B2 | 11/2003 | Edell et al. |
| 6,652,096 B1 | 11/2003 | Morris et al. |
| 6,667,471 B2 | 12/2003 | Bos et al. |
| 6,682,195 B2 | 1/2004 | Dreher |
| 6,705,729 B2 | 3/2004 | Piers et al. |
| 6,709,105 B2 | 3/2004 | Menezes |
| 6,709,107 B2 | 3/2004 | Jiang et al. |
| 6,709,108 B2 | 3/2004 | Levine et al. |
| 6,738,199 B2 | 5/2004 | Nishioka |
| 6,768,536 B2 | 7/2004 | Okuwaki et al. |
| 6,774,871 B2 | 8/2004 | Birdwell |
| 6,778,246 B2 | 8/2004 | Sun et al. |
| 6,793,340 B1 | 9/2004 | Morris et al. |
| 6,833,938 B2 | 12/2004 | Nishioka |
| 6,840,619 B2 | 1/2005 | Dreher |
| 6,851,805 B2 | 2/2005 | Blum et al. |
| 6,859,333 B1 | 2/2005 | Ren et al. |
| 6,883,916 B2 | 4/2005 | Menezes |
| 6,886,938 B1 | 5/2005 | Menezes |
| 6,893,124 B1 | 5/2005 | Kurtin |
| 6,894,751 B2 | 5/2005 | Payne et al. |
| 6,902,271 B2 | 6/2005 | Perrott et al. |
| 6,918,670 B2 | 7/2005 | Blum et al. |
| 6,948,818 B2 | 9/2005 | Williams et al. |
| 6,951,391 B2 | 10/2005 | Morris et al. |
| 6,955,433 B1 | 10/2005 | Wooley et al. |
| 6,956,682 B2 | 10/2005 | Wooley |
| 6,976,982 B2 | 12/2005 | Santini et al. |
| 6,986,579 B2 | 1/2006 | Blum et al. |
| 7,008,054 B1 | 3/2006 | Kurtin et al. |
| 7,009,757 B2 | 3/2006 | Nishioka et al. |
| 7,019,890 B2 | 3/2006 | Meredith et al. |
| 7,041,133 B1 | 5/2006 | Azar |
| 7,085,065 B2 | 8/2006 | Silver |
| 7,133,172 B2 | 11/2006 | Nishioka |
| 7,137,702 B2 | 11/2006 | Piers et al. |
| 7,159,981 B2 | 1/2007 | Kato |
| 7,159,983 B2 | 1/2007 | Menezes et al. |
| 7,195,353 B2 | 3/2007 | Blum et al. |
| 7,209,097 B2 | 4/2007 | Suyama |
| 7,229,173 B2 | 6/2007 | Menezes et al. |
| 2001/0055094 A1 | 12/2001 | Zhang |
| 2002/0140899 A1 | 10/2002 | Blum et al. |
| 2002/0149739 A1 | 10/2002 | Perrott et al. |
| 2002/0186346 A1 | 12/2002 | Stantz et al. |
| 2003/0018383 A1 | 1/2003 | Azar |
| 2003/0112523 A1 | 6/2003 | Daniell |
| 2003/0151721 A1 | 8/2003 | Lai et al. |
| 2003/0199978 A1 | 10/2003 | Lindsey et al. |
| 2003/0210377 A1 | 11/2003 | Blum et al. |
| 2004/0008319 A1 | 1/2004 | Lai et al. |
| 2004/0108971 A1 | 6/2004 | Waldern et al. |
| 2004/0117011 A1 | 6/2004 | Aharoni et al. |
| 2004/0130677 A1 | 7/2004 | Liang et al. |
| 2004/0179280 A1 | 9/2004 | Nishioka |
| 2004/0196435 A1 | 10/2004 | Dick et al. |
| 2004/0246440 A1 | 12/2004 | Andino et al. |
| 2005/0073739 A1 | 4/2005 | Meredith |
| 2005/0099594 A1 | 5/2005 | Blum et al. |
| 2005/0113912 A1 | 5/2005 | Feenestra et al. |
| 2005/0124983 A1 | 6/2005 | Frey et al. |
| 2006/0044510 A1 | 3/2006 | Williams et al. |
| 2006/0095128 A1 | 5/2006 | Blum et al. |
| 2006/0113054 A1 | 6/2006 | Silvestrini |
| 2006/0122531 A1 | 6/2006 | Goodall et al. |
| 2006/0164593 A1 | 7/2006 | Peyghambarian |

FOREIGN PATENT DOCUMENTS

| | | |
|---|---|---|
| DE | 4223395 | 1/1994 |
| EP | 0154962 | 9/1985 |
| EP | 0233104 | 8/1987 |
| EP | 0237365 | 9/1987 |
| EP | 0578833 | 1/1994 |
| EP | 0649044 | 4/1995 |
| EP | 0918248 | 5/1999 |
| EP | 0 578 833 | 1/2004 |
| GB | 2169417 | 7/1986 |
| GB | 2170613 | 8/1986 |
| JP | 55-076323 | 6/1980 |
| JP | 61156227 | 7/1986 |
| JP | 1-237610 | 9/1989 |
| JP | 05-100201 | 4/1993 |
| JP | 7-28002 | 1/1995 |
| JP | 11352445 | 12/1999 |
| JP | 2007-323062 | 12/2007 |
| WO | WO 92/01417 | 2/1992 |
| WO | WO 93/21010 | 10/1993 |
| WO | WO 97/06751 | 2/1997 |
| WO | WO 98/27863 | 7/1998 |
| WO | WO 99/27334 | 6/1999 |
| WO | WO 03/007851 | 1/2003 |
| WO | WO 03/050472 | 6/2003 |
| WO | WO 03/068059 | 8/2003 |
| WO | WO 2004/008189 | 1/2004 |
| WO | WO 2004/015460 | 2/2004 |
| WO | WO 2004/015481 | 2/2004 |
| WO | WO 2004/034095 | 4/2004 |
| WO | WO 2004/072687 | 8/2004 |

OTHER PUBLICATIONS

Office Action issued in the related U.S. Appl. No. 11/261,035, mailed Aug. 7, 2009.

International Search Report and Written Opinion in Application PCT/US05/39101 mailed Jul. 7, 2006.

International Search Report in Application PCT/US08/51649 mailed Jul. 7, 2008.

International Search Report corresponding to the PCT/US09/037544 application mailed May 20, 2009.

Supplementary European Search Report in Application EP 05824718 mailed Nov. 19, 2007.

International Search Report for application PCT/US 08/54721 mailed Aug. 20, 2008.

Tarascon et al., "Issues and challenges facing rechargeable lithium batteries" *Nature* 2001 414:359-367 (Nov. 15, 2001).

Kowel, Stephen T., et al "Focusing by electrical modulation of refraction in a liquid crystal cell" *Applied Optics* 23:2 (Jan. 15, 1984).

Thibos, Larry N., et al. "Vision through a liquid-crystal spatial light modulator" *Adaptive Optics Conference*; Durham, UK (1999).

Miller, Donald T., et al. "Requirements for Segmented Spatial Light Modulators For Diffraction-Limited Imaging Through Aberrated Eyes" Adaptive Optics for Industry and Medicine (1999).

Thibos, Larry N., et. al. "Use of Liquid-Crystal Adaptive-Optics to Alter the Refractive State of the Eye; Optometry and Vision Science" 74:7; *American Academy of Optometry* (Jul. 1997).

Thibos, Larry N., et. al. "Electronic Spectacles for the 21 Century" *Indian Journal of Optometry*, 2:1 (Spring 1999).

Bradley, Arthur "Profile: Larry N. Thibos, PhD., and Donald T. Miller, PhD." *Indiana Journal of Optometry*; 2:1 (Spring 1999).

Naumov, A.F. "Control Optimization of Spherical Modal Liquid Crystal Lenses", Optics Express 4:9; Optical Society of America (Apr. 26, 1999).

Naumov, A.F. "Liquid Crystal Adaptive Lenses with Modal Control" *Optics Letters*, 23:13 Optical Society of America (Jul. 1, 1998).

Optics, Org, Dec. 19, 2006 "Liquid Lenses Eye Commercial Breakthrough" Opto & Laser Europe (Nov. 2003).

Anderson, M. "Adaptive Optics: Liquid Crystals Lower the Cost of Adaptive Optics" *Laser Focus World* (Dec. 1999).

Davis, Robert A. "Computer Vision Syndrome—The Eyestrain Epidemic" *Review of Optometry* (Sep. 15, 1997).

Lazarus, Stuart M. "The Use of Yoked Base-Up and Base-In Prism for Reducing Eye Strain at the Computer" *Journal of the American Optometric Association* (Apr. 1996).

Eyecare Business (Oct. 1997).

\* cited by examiner

+ Center of transparent annular electrode structure o Center of transparent substrate Stack of electro-active elements Electro-active element with arrangement A
Electro-active element with arrangement B
Electro-active element with arrangement C
Electro-active element with arrangement D
Electro-active element with arrangement E

ADVANCED ELECTRO-ACTIVE OPTIC DEVICE

CROSS-REFERENCES TO RELATED APPLICATIONS

This application is a continuation in part of U.S. application Ser. No. 12/035,779, filed Feb. 22, 2008, which claims priority from U.S. Ser. No. 60/902,866 filed on Feb. 23, 2007, U.S. Ser. No. 61/020,759 filed on Jan. 14, 2008, U.S. Ser. No. 61/025,348 filed on Feb. 1, 2008, and U.S. Ser. No. 61/029,469 filed on Feb. 18, 2008, each of which is incorporated by reference in its entirety. This application claims the benefit of U.S. Ser. No. 61/037,351 filed on Mar. 18, 2008 and U.S. Ser. No. 61/060,291 filed on Jun. 10, 2008, each of which is incorporated by reference in its entirety.

BACKGROUND OF THE INVENTION

1. Field of the Invention

The present invention relates to an intraocular optic, an intraocular lens, a corneal inlay, and a corneal onlay. More specifically, the present invention relates to an intraocular optic, an intraocular lens, a corneal inlay, and a corneal onlay having an apodization mask and/or a dynamic aperture for increasing depth of field. The mask and/or aperture may be in optical communication or integral with an ophthalmic lens that at least partially corrects a conventional error (lower order aberrations such as myopia, hyperopia, regular astigmatism, and presbyopia) and/or a non-conventional error (such as higher order aberrations) of a user's eye.

2. Description of the Related Art

There are two major conditions that affect an individual's ability to focus on near and intermediate distance objects: presbyopia and aphakia. Presbyopia is the loss of accommodation of the crystalline lens of the human eye that often accompanies aging. In a presbyopic individual, this loss of accommodation first results in an inability to focus on near distance objects and later results in an inability to focus on intermediate distance objects. It is estimated that there are approximately 90 million to 100 million presbyopes in the United States. Worldwide, it is estimated that there are approximately 1.6 billion presbyopes. Aphakia is the absence of the crystalline lens of the eye, usually due to surgical removal during cataract surgery. In an aphakic individual, the absence of the crystalline lens causes a complete loss of accommodation that results in an inability to focus on either near or intermediate distance objects. For all practical purposes, an individual will get cataracts if he or she lives long enough. Furthermore, most individuals with cataracts will have a cataract operation at some point in their lives. It is estimated that approximately 1.2 million cataract surgeries are performed annually in the United States.

The standard tools for correcting presbyopia are reading glasses, multifocal ophthalmic lenses, and monocular fit contact lenses. Reading glasses have a single optical power for correcting near distance focusing problems. A multifocal lens is a lens that has more than one focal length (i.e., optical power) for correcting focusing problems across a range of distances. Multifocal lenses are used in eyeglasses, contact lenses, corneal inlays, corneal onlays, and intraocular lenses (IOLs). Multifocal ophthalmic lenses work by means of a division of the lens's area into regions of different optical powers. Multifocal lenses may be comprised of continuous surfaces that create continuous optical power as in a Progressive Addition Lens (PAL). Alternatively, multifocal lenses may be comprised of discontinuous surfaces that create discontinuous optical power as in bifocals or trifocals. Monocular fit contact lenses are two contact lenses having different optical powers. One contact lens is for correcting mostly far distance focusing problems and the other contact lens is for correcting mostly near distance focusing problems.

The standard tool for correcting aphakia is an intraocular lens (IOL). A first type of IOL is a single vision or multifocal IOL that is non-accommodating and cannot change its optical power. A second type of IOL is an accommodating IOL that can alter its focusing power by way of example only, compression, translation, mechanical bending of a surface, or a combination of the above. Aphakia may also be corrected by using a single vision IOL in one eye and a multifocal or accommodating IOL in the other eye, or any combination thereof.

Alternate approaches are also being used to correct presbyopia. One approach is a corneal inlay that provides a small, fixed diameter aperture. By way of example only, the ACI 7000 corneal inlay made by AcuFocus is approximately 3.8 mm in diameter, 10 μm thick, and contains an opaque annulus with a 1.6 mm diameter transparent opening. This opening acts to reduce the aperture of the human eye to a smaller diameter than what is normally achievable by the natural constriction of the pupil.

As is well known in the art, limiting the diameter of the aperture of an optical system increases the system's depth of field. Depth of field is the distance in front of and behind the object plane that appears to be in focus on the image plane. Although an optical system can only provide for the precise focus of an object at the focal distance, in a system with increased depth of field, the decrease in sharpness on either side of the focal distance is gradual. Therefore, within the depth of field, the blurring produced on the image plane is imperceptible under normal viewing conditions. An aperture is used to increase depth of field by eliminating at least a portion of the light rays which make a large angle with the lens's optical axis (non-paraxial light rays). Non-paraxial light rays are only sharply focused when originating from objects located at the focal distance. For objects located at other distances, non-paraxial light rays have the highest deviation from the image plane. By eliminating non-paraxial light rays, the deviation from the image plane is minimized and objects located within a fixed distance of the focal distance (i.e., within the depth of field) appear in focus.

The small aperture counteracts some of the effects of presbyopia by creating a larger range of distances that appear in focus and allows presbyopes to conduct near vision tasks without the need for multifocal contact or spectacle lenses. The ACI 7000 is manufactured from bio-compatible materials whose optical properties are static, such as polyvinyldene fluoride or non-hydrogel microporous perflouroether, by way of example only. As such, once the inlay is placed within the cornea its refractive optical power is fixed.

The AcuFocus corneal inlay is designed to reduce the amount of light which reaches the retina. Additionally, the inlay is usually only be implanted in one eye as deleterious optical effects such as halos, doubling of vision, light scattering, glare, loss of contrast sensitivity, and/or reduction of light hitting the retina are too great and may be unacceptable when the inlay is implanted in both eyes. These deleterious effects are caused by the size of the inlay's aperture and occluded annulus in relation to the size of the pupil. These effects especially occur at night when the pupil dilates.

Another approach for correcting presbyopia is corneal refractive surgery in which one eye is corrected for far distance and the other eye is corrected for near distance. Another approach is a corneal inlay that provides a multifocal effect using diffractive optics, for example.

However, each of these approaches for correcting presbyopia and/or aphakia has drawbacks. Of course, some of these drawbacks are more severe than others. For example, while spectacle eyewear is capable of correcting one's vision for far, near and intermediate distances, this approach requires wearing a device that takes away from one's natural appearance. Also, in some cases, certain multifocal lenses may cause the user to perceive distortion and experience vertigo.

Approaches for correcting presbyopia and/or aphakia that include the use of contact lenses can cause discomfort and can also result in one or more of: halos, doubling of vision, light scattering, glare, loss of contrast sensitivity, limited range of focus, and/or reduction of light hitting the retina. Approaches that include the use of IOLs can result in one or more of: light scattering, glare, halos, ghosting, loss of contrast sensitivity, limited range of focus, and/or reduction of light hitting the retina.

These drawbacks, or compromises to one's vision, can be very problematic especially, by way of example only, when driving at night, driving in the rain, or working on a computer. Therefore, there is a need for a superior mode of correction for presbyopia and/or aphakia.

BRIEF SUMMARY OF THE INVENTION

An ophthalmic device as described herein may include an aperture, a peripheral region, a first transparent electrode having a plurality of pixel regions and a second transparent electrode disposed over the first transparent electrode, and an electro-active layer disposed between the first electrode and the second electrode, the electro-active layer including a material that allows for a variable transmission of light. The pixel regions may be individually addressable. The optical transmission of the aperture, the peripheral region, or both may be adjustable. The shape of the aperture may be adjustable to various shapes and diameters, including shapes other than a circle, and the aperture may be positioned relative to the line of sight of a user of the device. The aperture also may be repositioned after the device has been applied to the user's eye. The device may be worn binocularly by the wearer, and may be capable of correcting higher order aberrations of the wearer's vision. When worn, the device may be fixed in position relative to the wearer's pupil.

An ophthalmic device as described herein may include an apodization mask constructed from an electro-active, transparent substrate, where the substrate has at least one optical transmission property that is alterable by electrical activation. The adjustable optical transmission property may be, for example, the index of refraction of the substrate, or the amplitude and/or phase of transmitted light. The device may include a dynamic aperture, where the shape and size of the aperture may be defined based on a modulation transfer function of the wearer's eye, and the geometry of the aperture may be remotely adjustable. The apodization mask may provide a transmission profile, such as a phase/amplitude profile, associated with a retinal image quality for distance vision and an ambient light level range. When worn, the device may be fixed in position relative to the wearer's pupil.

An ophthalmic device as described herein may include an apodization mask having a transparent substrate, where the substrate has at a refractive index gradient. The device may include a dynamic aperture which may be remotely adjustable. When worn, the device may be fixed in position relative to the wearer's pupil.

An ophthalmic device as described herein may include a substrate and a liquid crystal layer capable of altering the optical transmission of the device, typically by about 30%-99% upon electrical activation. The liquid crystal layer may be pixilated, and the device may include a controller capable of activating segments of the liquid crystal layer in a desired pattern. When worn, the device may be fixed in position relative to the wearer's pupil.

BRIEF DESCRIPTION OF THE DRAWINGS

Aspects and features of the invention will be understood and appreciated more fully from the following detailed description in conjunction with the figures, which are not to scale, in which like reference numerals indicate corresponding, analogous or similar elements.

DETAILED DESCRIPTION OF THE INVENTION

Figure 1:
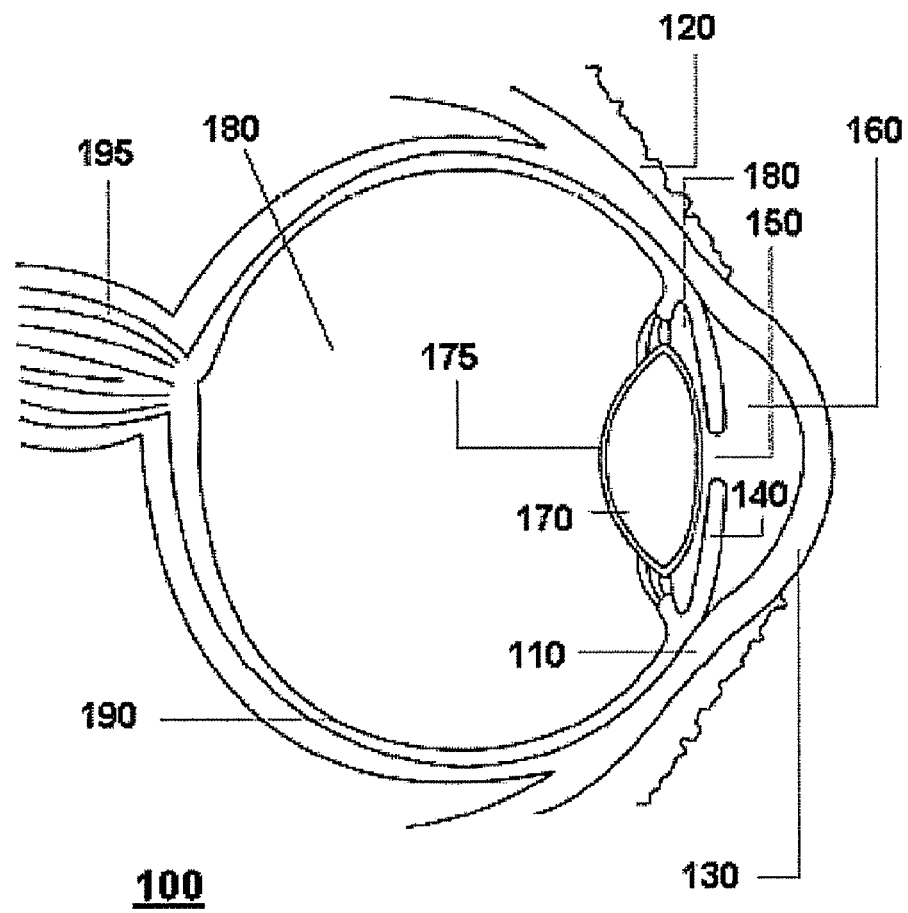
FIG. 1 shows a cross section of a healthy human eye.

As used herein, an electro-active element refers to a device with an optical property that is alterable by the application of electrical energy. The alterable optical property may be, for example, optical power, focal length, diffraction efficiency, depth of field, optical transmittance, tinting, opacity, refractive index, chromatic dispersion, or a combination thereof. An electro-active element may be constructed from two substrates and an electro-active material disposed between the two substrates. The substrates may be shaped and sized to ensure that the electro-active material is contained within the substrates and cannot leak out. One or more electrodes may be disposed on each surface of the substrates that is in contact with the electro-active material. The electro-active element may include a power supply operably connected to a controller. The controller may be operably connected to the electrodes by way of electrical connections to apply one or more voltages to each of the electrodes. When electrical energy is applied to the electro-active material by way of the electrodes, the electro-active material's optical property may be altered. For example, when electrical energy is applied to the electro-active material by way of the electrodes, the electro-active material's index of refraction may be altered, thereby changing the optical power of the electro-active element.

The electro-active element may be embedded within or attached to a surface of an ophthalmic lens to form an electro-active lens. Alternatively, the electro-active element may be embedded within or attached to a surface of an optic which provides substantially no optical power to form an electro-active optic. In such a case, the electro-active element may be in optical communication with an ophthalmic lens, but separated or spaced apart from or not integral with the ophthalmic lens. The ophthalmic lens may be an optical substrate or a lens. A "lens" is any device or portion of a device that causes light to converge or diverge (i.e., a lens is capable of focusing light). A lens may be refractive or diffractive, or a combination thereof. A lens may be concave, convex, or planar on one or both surfaces. A lens may be spherical, cylindrical, prismatic, or a combination thereof. A lens may be made of optical glass, plastic, thermoplastic resins, thermoset resins, a composite of glass and resin, or a composite of different optical grade resins or plastics. It should be pointed out that within the optical industry a device can be referred to as a lens even if it has zero optical power (known as plano or no optical power). However, in this case, the lens is usually referred to as a "plano lens". A lens may be either conventional or non-conventional. A conventional lens corrects for conventional errors of the eye including lower order aberrations such as myopia, hyperopia, presbyopia, and regular astigmatism. A non-conventional lens corrects for non-conventional errors of the eye including higher order aberrations that can be caused by ocular layer irregularities or abnormalities. The lens may be a single focus lens or a multifocal lens such as a Progressive Addition Lens or a bifocal or trifocal lens. Contrastingly, an "optic", as used herein, has substantially no optical power and is not capable of focusing light (either by refraction or diffraction). The term "refractive error" may refer to either conventional or non-conventional errors of the eye. It should be noted that redirecting light is not correcting a refractive error of the eye. Therefore, redirecting light to a healthy portion of the retina, for example, is not correcting a refractive error of the eye.

The electro-active element may be located in the entire viewing area of the electro-active lens or optic or in just a portion thereof. The electro-active element may be located near the top, middle or bottom portion of the lens or optic. It should be noted that the electro-active element may be capable of focusing light on its own and does not need to be combined with an optical substrate or lens.

FIG. 1 shows a cross section of a healthy human eye 100. The white portion of the eye is known as the sclera 110. The sclera is covered with a clear membrane known as the conjunctiva 120. The central, transparent portion of the eye that provides most of the eye's optical power is the cornea 130. The iris 140, which is the pigmented portion of the eye and forms the pupil 150. The sphincter muscles constrict the pupil and the dilator muscles dilate the pupil. The pupil is the natural aperture of the eye. The anterior chamber 160 is the fluid-filled space between the iris and the innermost surface of the cornea. The crystalline lens 170 is held in the lens capsule 175 and provides the remainder of the eye's optical power. A healthy lens is capable of changing its optical power such that the eye is capable of focusing at far, intermediate, and near distances, a process known as accommodation. The posterior chamber 180 is the space between the back surface of the iris and the front surface of the retina 190. The retina is the "image plane" of the eye and is connected to the optic nerve 195 which conveys visual information to the brain.

A static (non-dynamic) small aperture may have the benefit of a large depth of field but also has the detriment of decreased transmission of light through the lens or optic. Likewise, a static large aperture may have the benefit of increased transmission of light through the lens or optic but also has the detriment of a decreased depth of field.

An ophthalmic device (that may be a lens or an optic) may include an electro-active element having a dynamic aperture. As used herein, a dynamic aperture is an aperture having an alterable diameter. The aperture diameter of the dynamic aperture may be capable of switching between two or more diameters, for example, between a first diameter and a second diameter. The dynamic aperture may switch between diameters continuously (i.e., in a smooth transition) or discontinuously (i.e., in discrete steps). The dynamic aperture may have a minimum non-zero aperture diameter or may be capable of completely closing such that the aperture diameter is zero. The dynamic aperture may create apertures having a circular shape, an elliptical shape, or any shape.

A dynamic aperture may be capable of alternating between a decreased size for increased depth of field (and decreased transmission of light) and an increased size for increased transmission of light (and a decreased depth of field). The size of the dynamic aperture may be decreased for near distance and/or intermediate distance vision when a large depth of field is most beneficial to a user. The dynamic aperture may be increased in size from the diameter appropriate for proper near distance vision to a larger diameter appropriate for proper intermediate distance vision. The dynamic aperture's diameter may be further increased in size for proper far distance vision to provide for an increased transmission of light since a large depth of field is not critical for far distance vision.

As used herein, an aperture refers to a first region, typically at or near the entrance pupil, that is encompassed by a second region, which may be annular, where the second region has at least one optical characteristic different than the first region. For example, the second region may have a different optical transmission, refractive index, color, or optical path length than the first region. The second region may be referred to as a peripheral region. The optical properties of each region may remain constant within each region, or may vary based on the radius of the region or another function. An apodization function may be used to describe the variation in one or more optical properties of one or both regions.

An apodization mask may be used to alter light entering a wearer's eye. As used herein, a mask refers to a device that includes a controllable aperture. In some configurations, the mask operates by modulating the amplitude, phase, or both of light that is transmitted into the eye through the aperture. The aperture may be a static or a dynamic aperture. The mask may be a static mask, i.e., may always provide the same modulation of light such as where a static gradient of refractive index or optical transmittance is incorporated into a layer of the device, or it may be a dynamic mask that has an alterable index of refraction or optical transmittance.

As used herein, an intraocular optic (IOO) is an optic (having substantially no optical power) that is inserted or implanted in the eye. An intraocular optic may be inserted or implanted in the anterior chamber or posterior chamber of the eye, into the stroma of the cornea (similar to a corneal inlay), or into the epithelial layer of the cornea (similar to a corneal onlay), or within any anatomical structure of the anterior chamber of the eye. An intraocular optic has substantially zero optical power and therefore cannot focus light. Rather, an intraocular optic as described herein may have a dynamic aperture and may only be capable of providing an increased depth of field.

As used herein, an intraocular lens (IOL) is a lens (having optical power) that is inserted or implanted in the eye. An intraocular lens may be inserted or implanted in the anterior chamber or posterior chamber of the eye, into the capsular sac, or the stroma of the cornea (similar to a corneal inlay), or into the epithelial layer of the cornea (similar to a corneal onlay), or within any anatomical structure of the eye. An intraocular lens has one or more optical powers and may or may not also have a dynamic aperture. When the IOL has a dynamic aperture it may be capable of providing an increased depth of field.

As used herein, a corneal inlay is an optic (having substantially no optical power) or a lens (having optical power) that is inserted or implanted within the stroma of the cornea When referring specifically to a corneal inlay optic, the terms "corneal inlay optic" or "plano corneal inlay" may be used. When referring specifically to a corneal inlay lens, the terms "corneal inlay lens" or "focusing corneal inlay" may be used. As used herein, a corneal onlay is an optic (having substantially no optical power) or a lens (having optical power) that is inserted or implanted within the epithelium layer of the cornea. When referring specifically to a corneal onlay optic, the terms "corneal onlay optic" or "plano corneal onlay" may be used. When referring specifically to a corneal onlay lens, the terms "corneal onlay lens" or "focusing corneal onlay" may be used.

An electro-active element having a dynamic aperture may be integral with (i.e., embedded within or attached to) a corneal inlay, a corneal onlay, an IOO, or an IOL. The IOO or IOL may be inserted or implanted in the anterior chamber or posterior chamber of the eye, into the stroma of the cornea (as a corneal inlay), or into the epithelial layer of the cornea (as a corneal onlay). The corneal inlay and corneal onlay may be either a lens capable of focusing light (and therefore having an optical power) or an optic incapable of focusing light (and therefore having substantially no optical power). Electro-active elements as described herein may provide an increased depth of field, and may at least partially correct for a conventional and/or non-conventional error of a user's eye. Electro-active elements may be used in optical communication with one or more of the following devices which are capable of focusing light and may at least partially correct for a conventional and/or non-conventional error of a user's eye: a spectacle lens, a corneal inlay, a corneal onlay, or an intraocular lens. A dynamic aperture may provide for an increased depth of field and may be in optical communication and/or integral with an ophthalmic lens (which may be a single vision or multifocal lens) which corrects for refractive errors (such as presbyopia). A mostly continuous range of perceived focus from near distance to far distance may be achieved. For example, a dynamic aperture may provide increased depth of field which serves to provide a continuous range of focus between the fixed or static corrective powers of the ophthalmic lens). The mostly continuous range of focus may include the field from a near distance to a far distance, from a near distance to an intermediate distance, from an intermediate distance to a far distance, or between any range of distances.

Figure 2A:
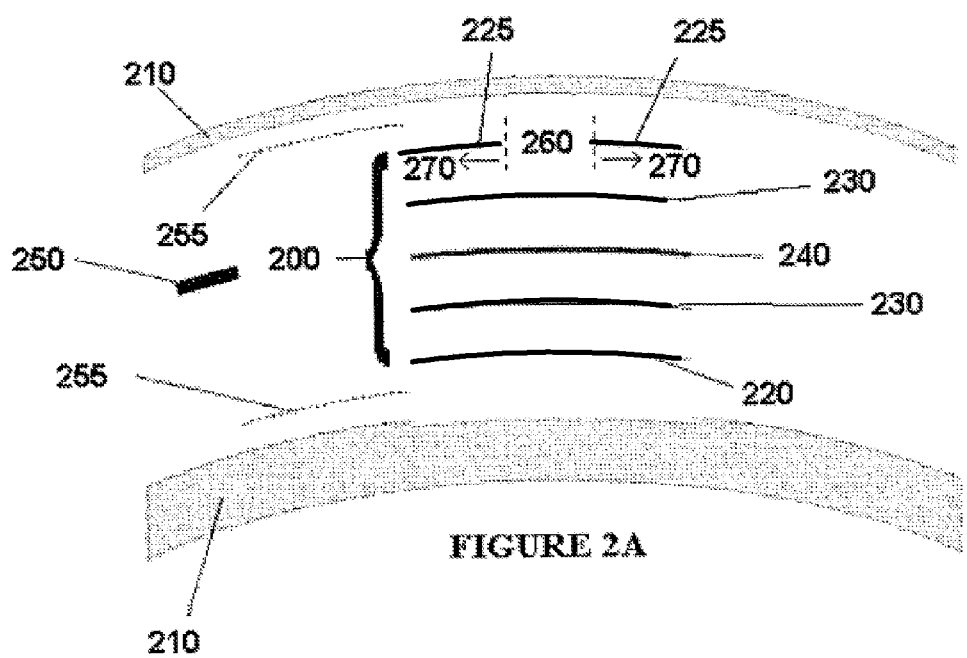
FIG. 2A shows an exploded cross-sectional side view of an electro-active element having a dynamic aperture.
Figure 2B:
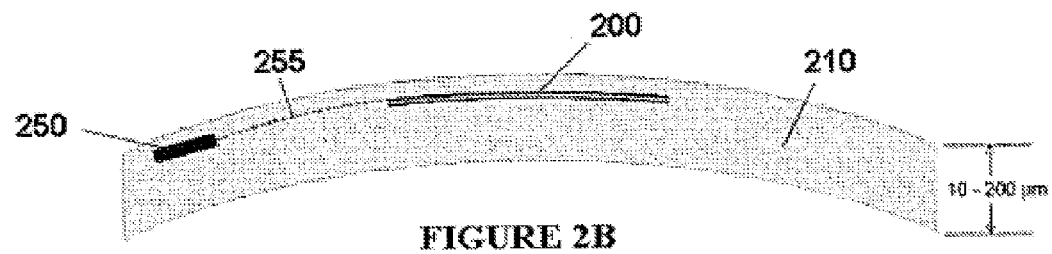
FIG. 2B shows a collapsed cross-sectional side view of the electro-active element of FIG. 2A.

FIG. 2A shows an exploded cross-sectional side view of an electro-active element 200 having a dynamic aperture. FIG. 2B shows a collapsed cross-sectional side view of the electro-active element of FIG. 2A. One or more electro-active elements 200 may be usable in a corneal inlay, a corneal onlay, an IOO, or an IOL. If more than one electro-active element is used, the electro-active elements may be stacked one upon another if there is proper insulation between the elements.

An electro-active element 200 may comprise two optical substrates 210 or may be bound by two optical substrates. The two substrates may be substantially flat and parallel, curved and parallel, or one substrate may have a surface relief diffractive pattern and the other substrate may be substantially smooth. The substrates may provide an optical power or the substrates may have no optical power. Each substrate may have a thickness of 200 µm or less and may be rigid or flexible. Example rigid substrate materials include glass and silicon. Example flexible substrates include flexible plastic films. In general, thinner substrates allows for a higher degree of flexibility for the electro-active element which may be important for lenses or optics that are inserted or implanted into the eye. A continuous optically transparent electrode 220 that provides for an electrical ground may be disposed on one of the substrates and one or more individually addressable optically transparent electrodes 225 may be disposed on the second substrate. Electrodes 225 may determine the properties of the dynamic aperture such as the size, shape, and/or diameters of the dynamic aperture. Electrodes 220 and 225 may, for example, comprise a transparent conductive oxide, such as indium tin oxide (ITO) or a conductive organic material (such as PEDOT:PSS or carbon nano-tubes). The thickness of the optically transparent electrodes may be, for example, less than 1 µm, but is preferred to be less than 0.1 µm. The electrodes 220 and 225 may be coated with an alignment layer 230. Alternatively, only one of the electrodes is coated with the alignment layer. An electroactive material 240 is disposed between the alignment layers. The thickness of the electro-active material may be between 1 µm and 10 µm, but is preferably less than 5 µm. The electro-active material may be a liquid crystalline (LC) material.

A controller 250 connects to the electrodes 220 and 225 by electrical connections 255 and may generate an electric field between the electrodes by applying one or more voltages to each electrode. The controller may be part of the electro-active element, or it may be located outside the electro-active element and connect to the electrodes using electrical contact points in the electro-active element. The controller may be connected to a power source, sensors, or any other necessary electronics. In the absence of an electric field between the electrodes, the liquid crystal molecules align in the same direction as the alignment direction. In the presence of an electric field between the electrodes, the liquid crystal molecules orient in the direction of the electric field. In an electroactive element, the electric field is perpendicular to the alignment layer. Thus, if the electric field is strong enough, the orientation of the liquid crystal molecules will be perpendicular to the alignment direction. If the electric field is not strong enough, the orientation of the liquid crystal molecules will be in a direction somewhere between the alignment direction and perpendicular to the alignment direction. It should be noted that the substrates may be as wide as or wider than the electrodes, alignment layers, and electroactive material.

The electro-active element may have an aperture 260 through which light passes and an annulus 270 in which light is absorbed and/or scattered. A change in the size of the dynamic aperture is typically inversely proportional to a change in the depth of field of the electro-active element and is dependent upon a change in the transmission of light through the electroactive element, as is known in the art. The aperture may be dynamic and may be capable of switching between one or more diameters. The annulus may be positioned at the peripheral edge of the electro-active element or may be spaced from the peripheral edge. The annulus may extend to the radial center of the electro-active element. The aperture may be positioned at the geometric center of the electro-active element and may be capable of extending all the way to the peripheral edge of the electro-active element, to a fixed distance from the peripheral edge, or to a radial distance from the geometric center of the electro-active element. The aperture also may be capable of being relocated such that the center of the aperture is not the same as the geometric center of the electro-active element. The annulus typically frames the aperture and defines the inner and outer limits and the size of the aperture. As is described in further detail herein, the aperture may be altered to achieve any of a continuous or discrete range of shapes and/or diameters.

The electro-active material may include a layer of liquid crystal doped with a dye material such as a dichroic dye. By doping the liquid crystal molecules with the dye material, the dye molecules align themselves with the liquid crystal molecules. The dye molecules are polar and rotate to align with an applied electrical field. The optical absorption of the dye material depends on the orientation of the individual dye molecules with respect to an incident optical wave. In a deactivated state with homogeneous (horizontal) alignment of the liquid crystal molecules, when the electric field between the electrodes is not strong enough, the dye molecules align with the alignment layers and the absorption of light through the liquid crystal is minimized or maximized, depending upon the relative orientation between the dipole moment and the direction of orientation of the dye molecule. In an activated state with homogeneous (horizontal) alignment of the liquid crystal molecules, when the electric field between the electrodes is strong enough, the dye molecules rotate and align with the orientation of the electric field, perpendicular to the alignment direction. In this orientation, the absorption of light though the liquid crystal is minimized. The opposite may be the case when a homeotropic (vertical) alignment of the liquid crystal is used such that absorption is minimized in a deactivated state and maximized in an activated state. A ferroelectric liquid crystalline material may also be used.

Figure 2C:
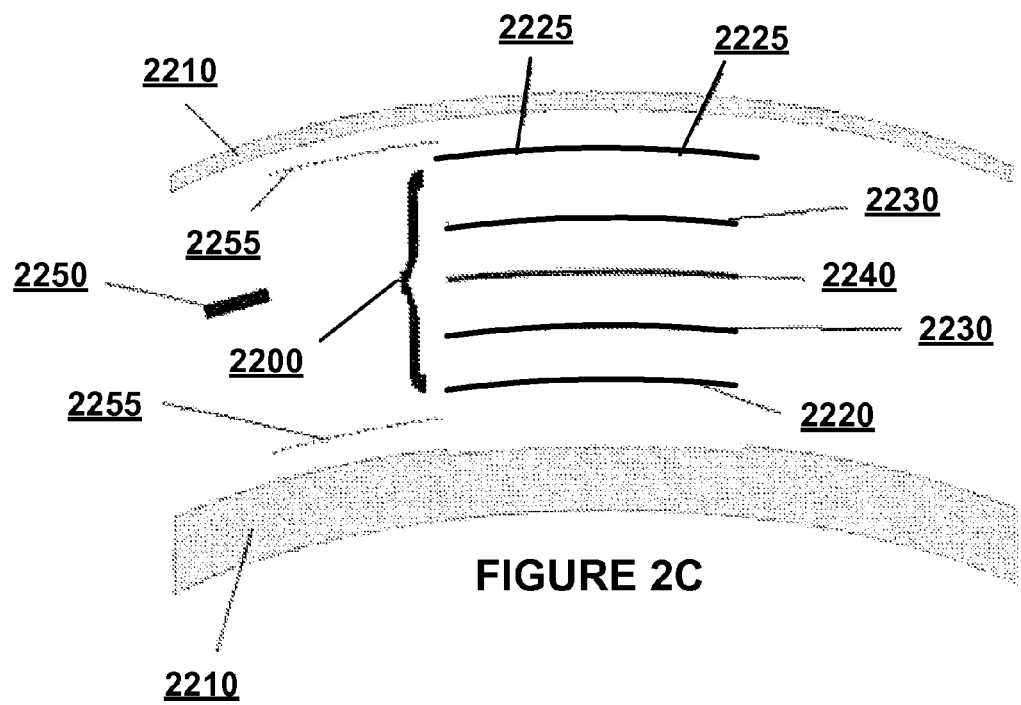
FIG. 2C shows an exploded cross-sectional side view of an element having an apodization mask.
Figure 2D:
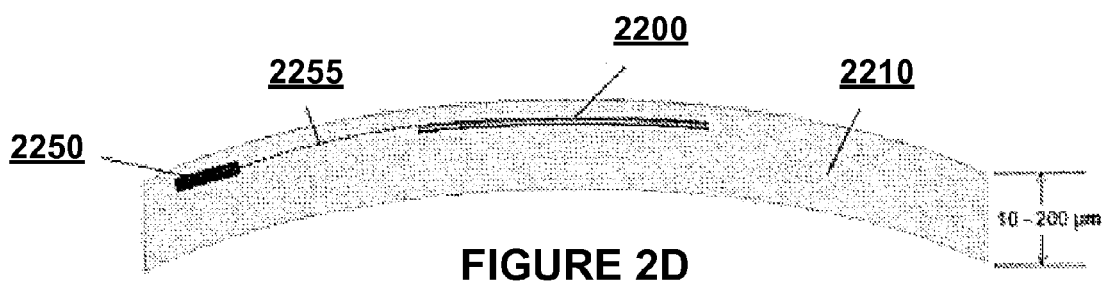
FIG. 2D shows a collapsed cross-sectional side view of the element of FIG. 2C.

FIG. 2C shows an exploded cross-sectional side view of an optical element 2200 having an apodization mask. FIG. 2D shows a collapsed cross-sectional side view of the element of FIG. 2C. One or more optical elements 2200 may be usable in a corneal inlay, a corneal onlay, an IOO, or an IOL. If more than one element is used, the elements may be stacked one upon another if there is proper insulation between the elements.

In one configuration, the apodization mask may include a single layer 2210 that includes a refractive index gradient. For example, the substrate 2210 may include a layer of a transparent polymer or other material that has a refractive index gradient, preferably of at least 0.01 units/mm in at least one meridian. In such a configuration, the other elements 2200, 2250, 2255 may be omitted. This configuration may be referred to as a static mask. As a specific example, the substrate 2210 may include at least one layer of a material, such as a transparent polymer, that includes a refractive index gradient. Preferably, the gradient is at least 0.01 units/mm in at least one meridian.

A dynamic apodization mask may include an electro-active element 2200 having two optical substrates 2210 or that is bound by two optical substrates. The two substrates may be substantially flat and parallel, curved and parallel, or one substrate may have a surface relief diffractive pattern and the other substrate may be substantially smooth. The substrates may provide an optical power or the substrates may have no optical power. Each substrate may have a thickness of 200 µm or less. In general, thinner substrates allows for a higher degree of flexibility for the electro-active element which may be important in optics or lenses that are inserted or implanted into the eye. A continuous optically transparent electrode 2220 that provides for an electrical ground may be disposed on one of the substrates and one or more individually addressable optically transparent electrodes 2225 may be disposed on the second substrate. Electrodes 2225 may determine the properties of the dynamic mask by altering the refractive index at various parts of the mask. The electrodes 2220, 2225 may include a transparent conductive oxide (such as ITO) or a conductive organic material (such as PEDOT:PSS or carbon nano-tubes). The thickness of the optically transparent electrodes may be, for example, less than 1 µm, but is preferred to be less than 0.1 µm. The electrodes 2220 and 2225 may be coated with an alignment layer 2230. Alternatively, only one of the electrodes is coated with the alignment layer. An electroactive material 2240 is disposed between the alignment layers. The thickness of the electro-active material may be between 1 µm and 10 µm, but is preferably less than 5 µm. The electro-active material may be a liquid crystalline material.

A controller 2250 connects to the electrodes 2220 and 2225 by electrical connections 2255 and is capable of generating an electric field between the electrodes by applying one or more voltages to each electrode. In some configurations, the controller is part of the electro-active element. The controller also may be located outside the electro-active element and connects to the electrodes using electrical contact points in the electro-active element. The controller may be connected to a power source, sensors, or any other necessary electronics. In the absence of an electric field between the electrodes, the liquid crystal molecules align in the same direction as the alignment direction. In the presence of an electric field between the electrodes, the liquid crystal molecules orient in the direction of the electric field. In an electro-active element, the electric field is perpendicular to the alignment layer. Thus, if the electric field is strong enough, the orientation of the liquid crystal molecules will be perpendicular to the alignment direction. If the electric field is not strong enough, the orientation of the liquid crystal molecules will be in a direction somewhere between the alignment direction and perpendicular to the alignment direction. It should be noted that the substrates may be as wide as or wider than the electrodes, alignment layers, and electroactive material.

The electro-active material may include a layer of liquid crystal doped with a dye material such as an electrochromic dye. By doping the liquid crystal molecules with the dye material, the dye molecules align themselves with the liquid crystal molecules. The dye molecules are polar and rotate to align with an applied electrical field. The optical properties of the dye material with respect to the eye depend on the orientation of the individual dye molecules with respect to an incident optical wave. In a deactivated state with homogeneous (horizontal) alignment of the liquid crystal molecules, when the electric field between the electrodes is not strong enough, the dye molecules align with the alignment layers and the index of refraction of the layer is unchanged by the dye. For example, the index of refraction in an unactivated region may be at a minimum. In an activated state with homogeneous (horizontal) alignment of the liquid crystal molecules, when the electric field between the electrodes is strong enough, the dye molecules rotate and align with the orientation of the electric field, perpendicular to the alignment direction. In this orientation, the dye alters the index of refraction of the region. For example, the index of refraction of an activated region may be at a maximum. The opposite may be the case when a homeotropic (vertical) alignment of the liquid crystal is used such that a deactivated state has a higher index of refraction an activated state has a lower index of refraction. A ferroelectric liquid crystalline material may also be used.

The liquid crystal may alter its refractive index over the visible spectrum by at least 0.1 units upon electrical activation. As used herein, the "visible spectrum" refers to light having a wavelength in the range of about 400-750 nm. A liquid crystal (LC) layer may include a guest-host mixture capable of altering the optical transmission of light upon electrical activation. As used herein, the optical transmission of a layer or device refers to the percentage of light energy that is transmitted through the layer or device and not lost to absorption or scattering. Preferably, the mixture is capable of altering the optical transmission by at least about 30%-99% upon activation. The liquid crystal layer may be pixilated as previously described, and may be electrically addressable in discrete portions of at least about 0.25 $\mu m^2$ without affecting the response of adjacent portions. The liquid crystal layer may be controllable by a computerized device, such as a processor and associated software, which may be capable of arbitrarily addressing multiple segments in a preprogrammed or adaptable manner. The software may be permanently embodied in a computer-readable medium, such as a special-purpose chip or a general purpose chip that has been configured for a specific use, or it may be provided by a digital signal. The software may be incorporated into a digital signal processing unit embedded into a vision correcting device that includes the apodization mask. The liquid crystal layer also may be configured or programmed to generate a pattern that changes or modulates the amplitude, phase, or both of light transmitted through the mask into the eye of the patient fitted with the mask or a vision-correcting device incorporating the mask.

The liquid crystalline material in FIGS. 2A-2D may be a nematic liquid crystal, a twisted nematic liquid crystal, a super-twisted nematic liquid crystal, a cholesteric liquid crystal, a smectic bi-stable liquid crystal, or any other type of liquid crystalline material. An alignment layer is a thin film, which, by way of example only, may be less than 100 nanometers thick and constructed from a polyimide material. The thin film is applied to the surface of substrates that comes into direct contact with liquid crystalline material. Prior to assembly of the electro-active element, the thin film is buffed in one direction (the alignment direction) with a cloth such as velvet. When the liquid crystal molecules come in contact with the buffed polyimide layer, the liquid crystal molecules preferentially lie in the plane of the substrate and are aligned in the direction in which the polyimide layer was rubbed (i.e., parallel to the surface of the substrate). Alternatively, the alignment layer may be constructed of a photosensitive material, which when exposed to linearly polarized 1N light, yields the same result as when a buffed alignment layer is used.

Figure 3A:
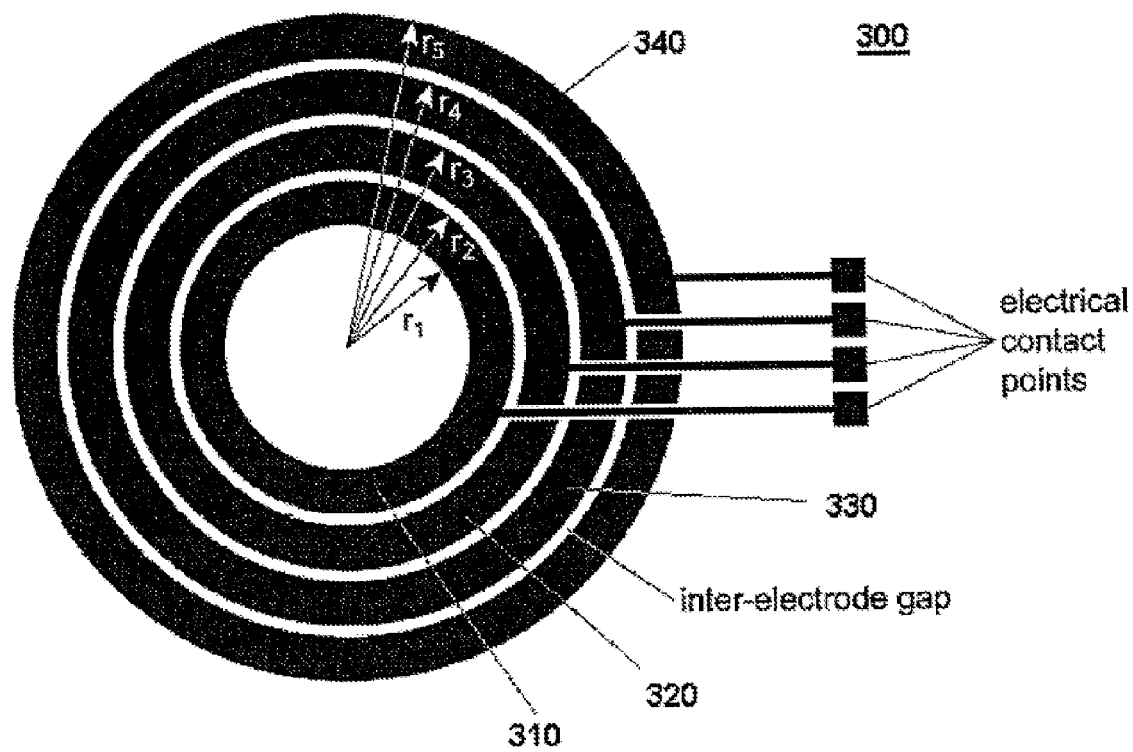
FIG. 3A shows a plurality of electrode rings operable for creating a dynamic aperture.

FIG. 3A shows a plurality of electrode rings 300 operable for creating a dynamic aperture. The electrode rings may be useful as optically transparent electrodes 225 in the electro-active element 200. The electro-active material 240 may be a liquid crystal doped with a dichroic dye. Electrode rings 300 may be composed of several annular shaped electrodes 310, 320, 330, and 340. Of course, fewer or more electrodes are possible. Each electrode is individually addressable. The center of the electrode rings may be concentric relative to a papillary axis once the electro-active element is placed in or on the eye. The inter-electrode gap may be approximately 5 μm to 10 μm but may be smaller. The inner diameter of electrode 310 is r1, the outer diameter of electrode 310 is r2, the outer diameter of electrode 320 is r3, the outer diameter of electrode 330 is r4, and the outer diameter of electrode 340 is r5. The inner diameter of each electrode may define a different aperture size.

An electrode may be "activated" if a sufficiently strong electric field is applied between the electrode and a ground electrode, if voltage above a threshold is applied to the electrode, or if a condition is satisfied which places an electro-active material between the electrode and the ground electrode in an activated state. An electrode may be "deactivated" if a sufficiently strong electric field is not applied between the electrode and a ground electrode, if voltage below a threshold is applied to the electrode, or if a condition is satisfied which places an electro-active material between the electrode and the ground electrode in a deactivated state.

When a liquid crystalline material is used, the liquid crystalline material may be activated when a voltage above a threshold of approximately 10 volts is applied between the electrodes and may be deactivated when a voltage below a threshold of approximately 10 volts is applied between the electrodes. The electric power used is that of approximately 1 microwatt. It should be pointed out that the electric potential can be, by way of example only, 1 volt or less, 5 volts or less, 10 volts or less, or over 10 volts.

To reduce power consumption, a bi-stable liquid crystalline material may be used. A bistable liquid crystalline material may switch between one of two stable states with the application of electrical power (with one state being an activated state and the other state being a deactivated state). The bi-stable liquid crystalline material remains in the one stable state until sufficient electrical power is applied to switch the bi-stable liquid crystalline material to the other stable state. Thus, electrical power is only needed to switch from one state to the other and not to remain in a state. The bi-stable liquid crystalline material may switch to a first state when +5 volts or more is applied between the electrodes and may switch to a second state when −5 volts or less is applied between the electrodes. Of course other voltages, both higher and lower, are possible.

If electrodes 310, 320, 330, and 340 are activated, an opaque annulus 270 may be formed between r1 and r5 and aperture 260 will be formed between the center of the electrodes and r1. If electrode 310 is deactivated, the opaque annulus will now be formed between the inner diameter of electrode 320 and r5 and aperture 260 will now be formed between the center of the electrodes and the inner diameter of electrode 320. If electrodes 310,320,330, and 340 are deactivated, there will be no opaque annulus 270 and aperture 260 will now be formed between the center of the electrodes and r5. The aperture may be increased by first deactivating electrode 310, then electrode 320, then electrode 330, and finally electrode 340. The aperture may be decreased by first activating electrode 340, then electrode 330, then electrode 320, and finally electrode 310. Thus, as shown in FIG. 3A, there are 5 possible aperture stops. However, fewer or more aperture stops are possible. As in a camera, each aperture stop may provide an aperture having twice the area of the next smallest aperture size. In other words, there may be a square root of two relationship between the inner diameters of each electrode. Of course, other aperture sizes are possible. When fully constricted, the aperture diameter may be between approximately 1.0 mm and approximately 3.0 mm, and may preferably be between approximately 1.0 mm and approximately 2.5 mm, and more preferably may be between approximately 1.0 mm and approximately 2.0 mm. When fully dilated, the aperture diameter may be approximately 7.0 mm or larger. In some configurations, there may be no aperture (i.e., there is no annulus such that the pupil of the eye serves as the natural aperture) in dark or dim environments.

The outer edge of the annulus may extend further than the outer edge of the pupil (whether fully dilated or constricted). If there is a gap between the outer edge of the annulus and the outer edge of the pupil deleterious effects may occur such as, by way of example only, halos, light scattering, and reduction in contrast sensitivity.

Each of the electrode rings may be activated approximately at the same time for an instantaneous change in the aperture. To produce a fading in and out effect which gradually reduces and enlarges the dynamic aperture, each of the electrode rings may be activated and/or deactivated sequentially. For example, the outermost electrode ring may be activated first and deactivated last and the innermost electrode ring may be activated last and deactivated first. The electrodes may be activated or deactivated in less than approximately 1 second, and may be preferably activated or deactivated in less than approximately 0.5 seconds.

The electrodes 225 may be a plurality of individually addressable electrodes arranged in a grid. Each electrode may be referred to a "pixel" (the electrodes in this case may be referred to as "pixilated"). The pixel may be any size or shape. By selectively electrically activating or deactivating the pixels the aperture 260 and annulus 270 may be formed.

Figure 3B:
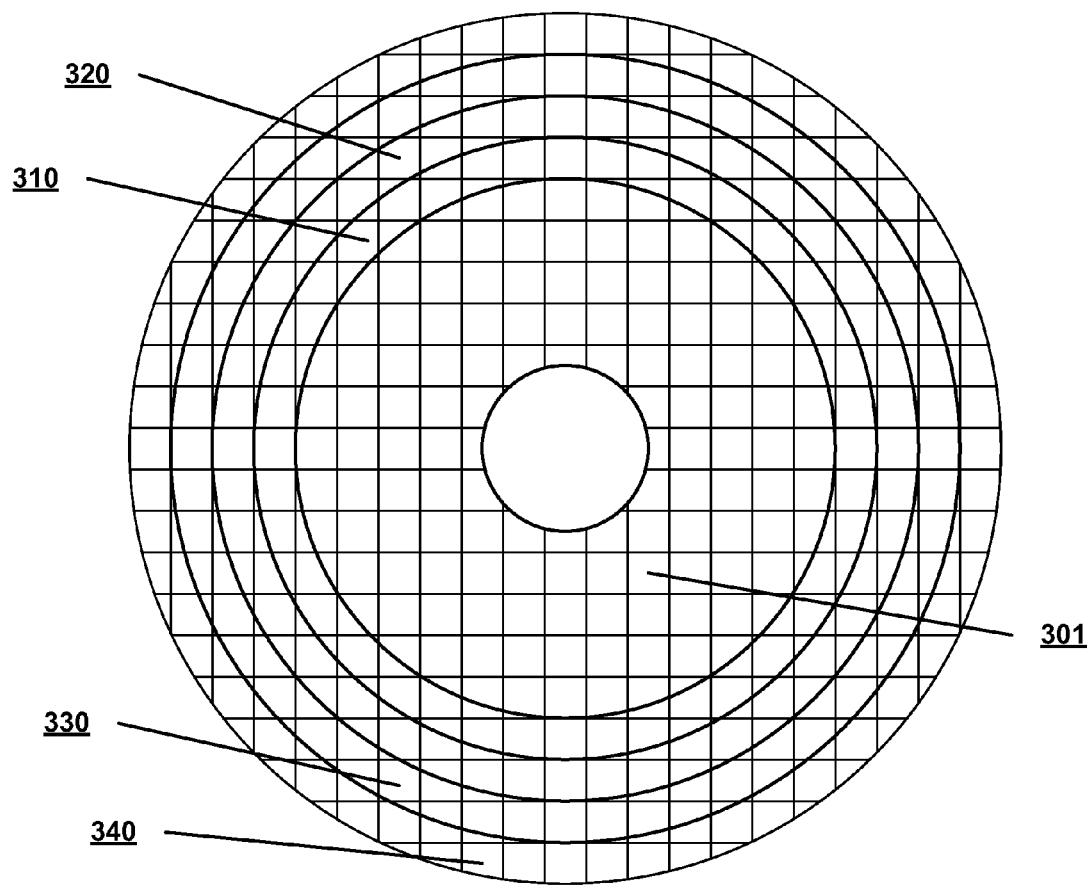
FIG. 3B shows an example of a dynamic aperture having pixilated electrodes operable for creating a dynamic aperture.
Figure 3C:
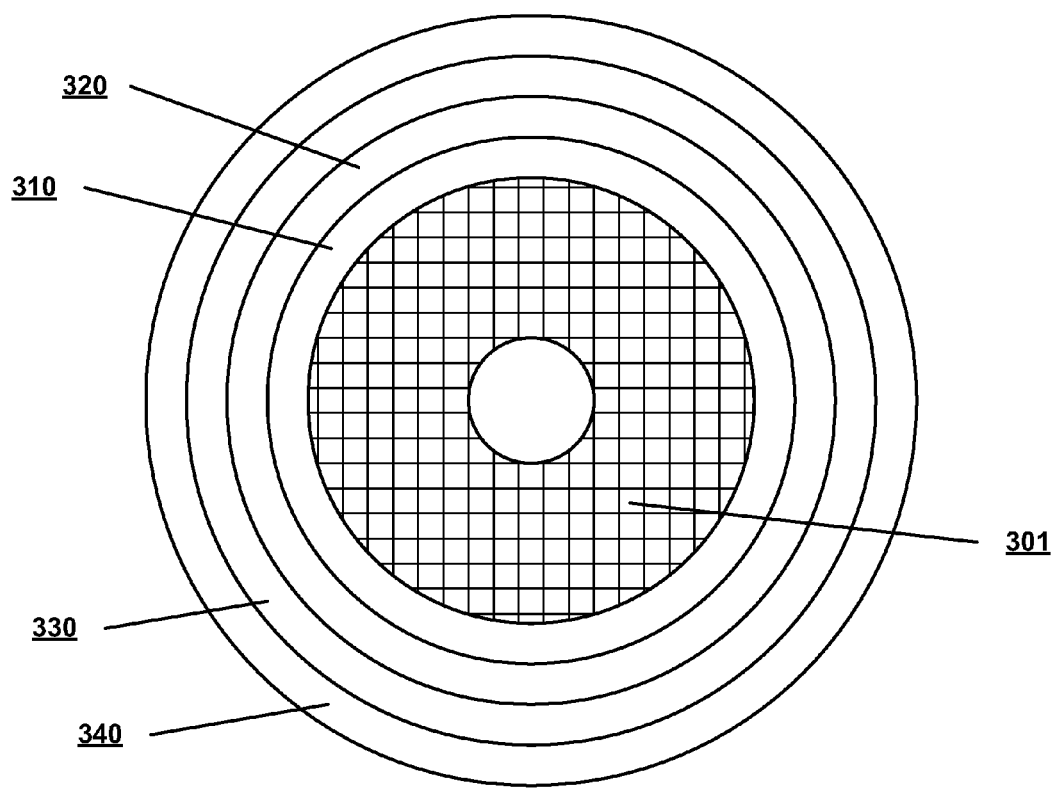
FIG. 3C shows an example of a dynamic aperture having pixilated electrodes operable for creating a dynamic aperture.
Figure 3D:
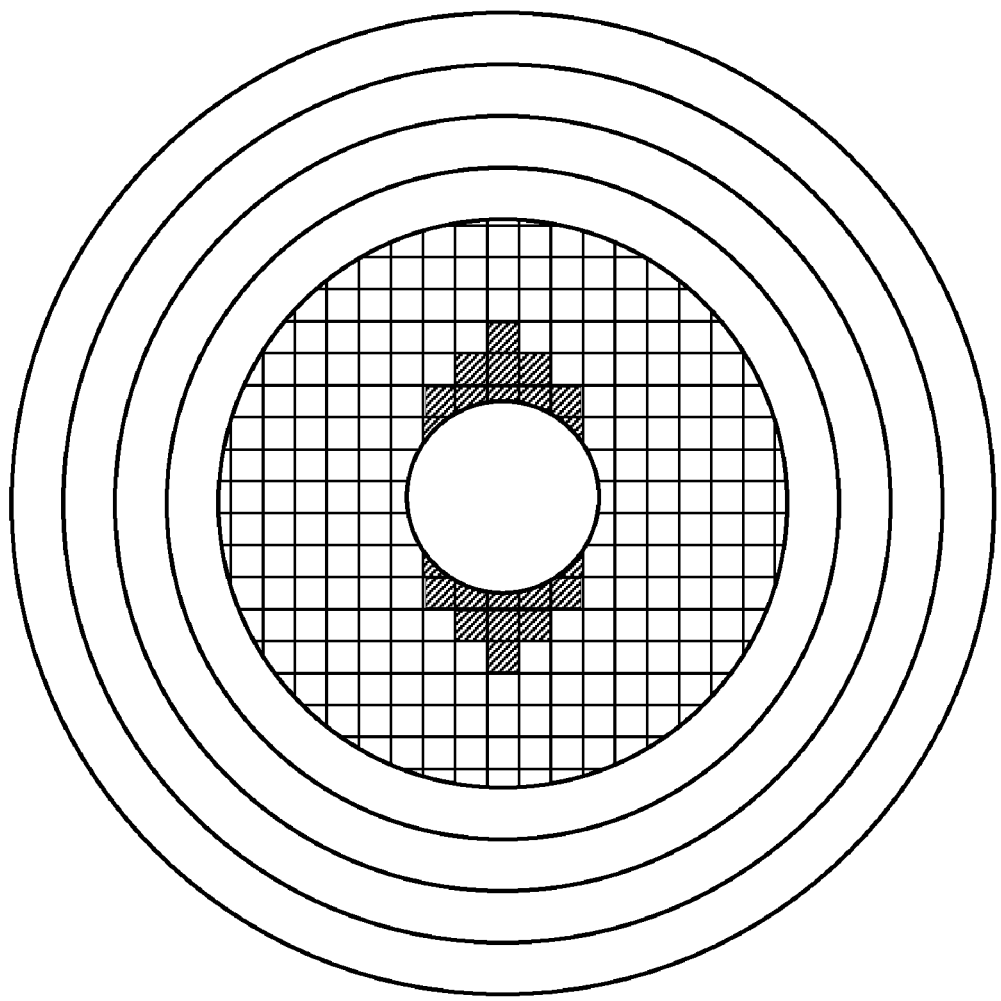
FIG. 3D shows an example of a dynamic aperture having pixilated electrodes operable for creating a dynamic aperture.

Some or all of the annular electrodes may be pixilated, or various portions of the electrode rings, an inner portion, or combinations thereof may be pixilated. FIGS. 3B and 3C show examples of pixilated electrodes. For example, FIG. 3B, shows a configuration in which each the electrode rings 310, 320, 330, 340 and an inner region 301 are pixilated. In some configurations, the electrode rings may be activated or deactivated as rings to provide an annulus of desired size, pixels in the inner region may be activated or deactivated to provide an aperture of desired shape and/or size. As another example, FIG. 3C shows a configuration in which only the inner region 301 is pixilated, and the electrode rings 310, 320, 330, 340 are not. By selectively activating or deactivating the pixels, an arbitrary shape and size may be provided for the annulus and aperture. As a specific example, by selectively activating or deactivating the shaded pixels 303 in FIG. 3D, a roughly-oval aperture may be formed. The specific set of shaded pixels is illustrative only, and other shapes and sizes may be formed by appropriate selection of pixels in the inner region and/or the electrode rings. As described in further detail herein, a specific aperture and/or annulus may be defined to match a user's specific needs, such as to optimize the modulation transfer function of the eye.

For example, an individual's subjective satisfaction with perceived image quality may be improved when the image quality is maximized over a low- to mid-frequency range. A subjective quality factor may be defined as $$SQF = \int_{10}^{40} \int_{0}^{2r} |\tau(f,\theta)| d(\log f) d\theta$$

Such a function is described in further detail in E. M. Granger and K. N. Cupery, "An Optical Merif Function (SQF) which Correlates with Subjective Judgments," Photogr. Sci. and Eng., v. 16 (3), 1972, p. 221-30. It has been found that the specific size and shape of an aperture to provide desirable improvements in subjective vision may be determined by minimizing the merit function (SQF) based on computation of a visual performance metric, such as visual strehl as a function of pupil size. Such a calculation may be performed using ray tracing of a specific eye model. Specific examples of models suitable for performing these calculations include the "Indiana Eye" model and the Liu Brennan eye model as known in the art.

Figure 4A:
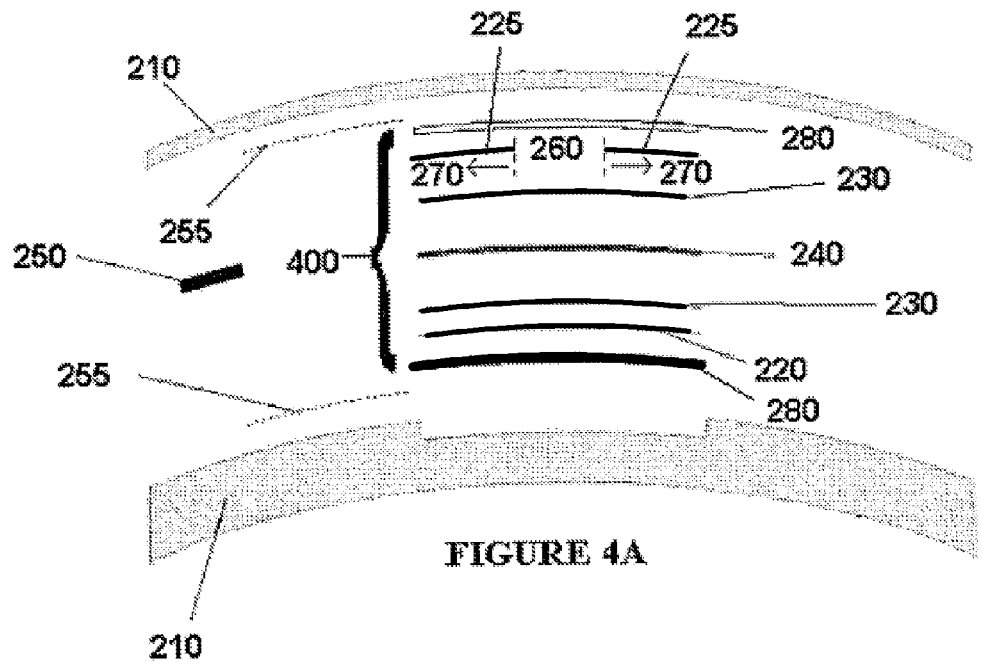
FIG. 4A shows an exploded cross-sectional side view of an electro-active element having a dynamic aperture.
Figure 4B:
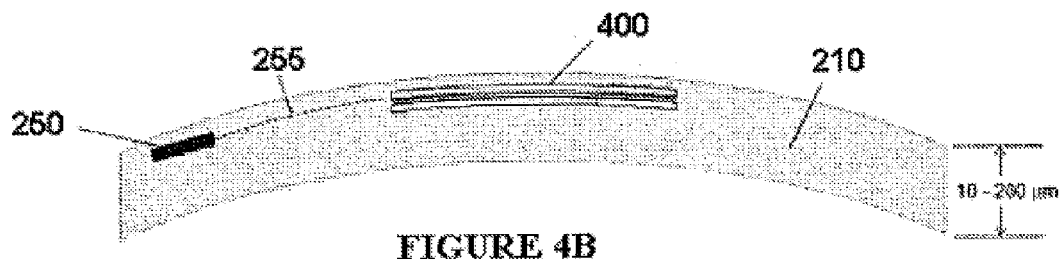
FIG. 4B shows a collapsed cross-sectional side view of the electro-active element of FIG. 4A.

FIG. 4A shows an exploded cross-sectional side view of an electroactive element 400 having a dynamic aperture. FIG. 4B shows a collapsed cross-sectional side view of the electroactive element of FIG. 4A. Similar to the electro-active element 200, electroactive element 400 includes two optical substrates 210. A continuous optically transparent electrode 220 that provides for an electrical ground may be disposed on one of the substrates and one or more individually addressable optically transparent electrodes 225 may be disposed on the second substrate. Electrodes 225 may determine the properties of the dynamic aperture such as the size, shape, and/or diameters of the dynamic aperture. The electrodes 220 and 225 may be coated with an alignment layer 230. The alignment layers have an alignment direction offset 90 degrees from each other, but other values such as 180, 270, 360 degrees or more are possible. An electroactive material 240 is disposed between the alignment layers. The electro-active material may be a liquid crystalline material, preferably one of a nematic, cholesteric, or smectic bi-stable liquid crystalline material. The liquid crystalline material may be doped with a dichroic dye and become a dichroic liquid crystalline material. A controller 250 connects to the electrodes 220 and 225 by electrical connections 255 and is capable of generating an electric field between the electrodes. The electro-active element may have an aperture 260 through which light passes and an annulus 270 in which light is absorbed and/or scattered. The electro-active element 400 may further include two polarizers 280 positioned on either side of the electro-active material (e.g., exterior to the electrodes). The polarizers may also be located on the outer surfaces of the substrates (the electrodes are located on the innermost surface of the substrates). Each of the polarizers may have a direction of polarization parallel to the director of the liquid crystal layer at their respective outer surfaces (i.e., parallel to the alignment direction of the closest alignment layer). The polarizers have relative directions of polarization offset by, for example, 90 degrees. Such offset polarizers may be referred to as "crossed" polarizers.

In a deactivated state, when the electric field between the electrodes is not strong enough, the alignment layers orient the director of the liquid crystal layer to align with the polarizers at the outer surfaces. In this orientation, light entering the first polarizer (i.e., light that is polarized parallel to the polarization direction of the first polarizer) is rotated 90 degrees by the liquid crystal and can now pass through the second polarizer (i.e., the light is now polarized parallel to the polarization direction of the second polarizer). Therefore, in a deactivated state the absorption of light through the electro-active element is minimized. In an activated state, when the electric field between the electrodes is strong enough, the liquid crystal molecules align with the orientation of the electric field, perpendicular to the alignment direction. In this orientation, light entering the first polarizer (i.e., light that is polarized parallel to the polarization direction of the first polarizer) is not rotated and is blocked by the second polarizer (i.e., the light is polarized orthogonal to the polarization direction of the second polarizer). Therefore, in an activated state the absorption of light though the liquid crystal is maximized.

The electrode rings shown in FIGS. 3A-D may be useful as optically transparent electrodes 225 in the electro-active element 400. As above, if electrodes 310, 320, 330, and 340 are activated, opaque annulus 270 will be formed between r1 and r5 and aperture 260 will be formed between the center of the electrodes and r1. If electrode 310 is deactivated, the opaque annulus will now be formed between the inner diameter of electrode 320 and r5 and aperture 260 will now be formed between the center of the electrodes and the inner diameter of electrode 320. If electrodes 310, 320, 330, and 340 are deactivated, there will be no opaque annulus 270 and aperture 260 will now be formed between the center of the electrodes and r5.

One drawback to using polarizing films may be that they typically absorb approximately 50% of incident light. Therefore, utilizing such films in an actual device would limit the amount of light that reaches the retina. To counteract this effect, a region concentric with the annular electrodes may be physically removed from one or both of the polarizers. The region removed may be or any size or shape, but in a preferred configuration is equal to the inner diameter of the smallest ring electrode. By removing this central region, one or more polarizers may be used while increasing the overall transmission through the electro-active element. In this configuration, the functionality of the dynamic aperture is not affected and overall transmission is increased. Additionally, the transmission contrast ratio (the ratio between light transmitted through the aperture and light transmitted through the annulus) between the aperture and the annulus is increased thereby making the dynamic aperture more efficient in providing depth of field. Instead of removing the region, the region may instead be composed of a thinner or less efficient polarizing film used to increase transmission, thereby favoring performance in the transmitting state over the opaque state. In each of these configurations, the transmission contrast ratio between the darkened area of the annulus and a region of the aperture may be increased.

It is virtually impossible to have an implanted corneal inlay, corneal onlay, IOO, or IOL perfectly centered with the optical axis of the eye, because the eye is asymmetric in normal anatomic configuration. The most desired position of an implant is aligned with the central axis of the pupil. Nevertheless, approximately 0.1 mm or 0.2 mm decentration of the eye relative to the center of the eye's pupil must be anticipated even under normal anatomical circumstances.

Figure 5:
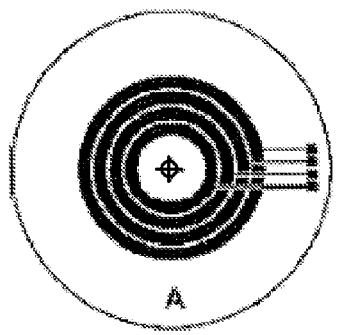
FIG. 5 shows several arrangements of the electrode rings shown in FIG. 3A herein the geometric center of a dynamic aperture may be repositioned relative to the geometric center of one's pupil.
Figure 6:
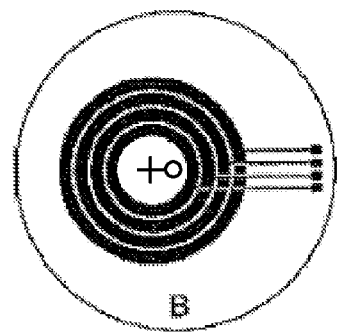
FIG. 6 shows a stack of five electro-active elements that may each be used for the different arrangements of ring electrodes shown in FIG. 5.
Figure 6:
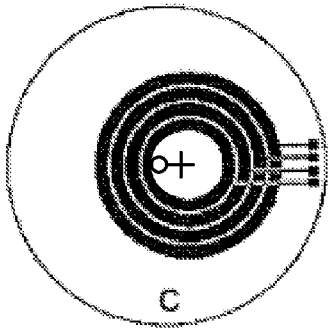
Figure 6:
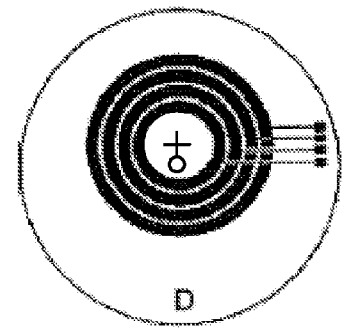
Figure 6:
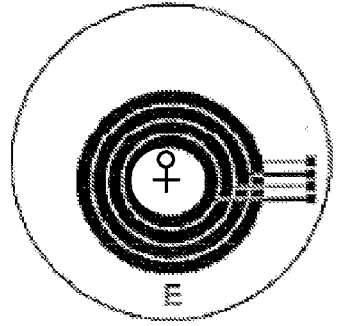
Figure 6:
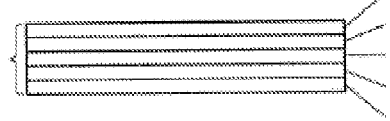

FIG. 5 shows several arrangements of the electrode rings shown in FIG. 3A in which the geometric center of a dynamic aperture may be repositioned relative to the geometric center of one's pupil. Arrangement A has the geometric center of the ring electrodes aligned with the geometric center of the electro-active element's substrates. Arrangements B, C, D, and E have the geometric center of the ring electrodes aligned to the left, to the right, above, and below, respectively, with the geometric center of the electro-active element's substrates. Arrangements A, B, C, D, and E may each be utilized in a separate electro-active element. FIG. 6 shows a stack of five electro-active elements that may each be used for the different arrangements of ring electrodes shown in FIG. 5. Each electro-active element is properly insulated from the other electro-active elements. The distance between the geometric center of the ring electrodes and the geometric center of the substrates may be between approximately 0.0 mm and approximately 1 mm, and more preferably between approximately 0.0 mm and approximately 0.5 mm. It should be noted that other alignments at any angle between the two centers are possible. This may allow for the ability to alter the center of the dynamic aperture by way of remote adjustment after an implant has been surgically implanted. One or more of the arrangements of ring electrodes may be activated to the exclusion of the other arrangement to re-align the center of the dynamic aperture relative to the line of sight of the user. This is important in cases where an implant was surgically implanted out of alignment with the line of sight of the user. Certain retinal diseases or trauma such as, by way of example only, macular degeneration, retinal tears, or retinal detachments may damage a region of the retina. This also may also be useful for realigning the line of sight of the user away from a damaged region of the retina to a healthy region of the retina.

The use of an aperture to block a part of the light entering the human pupil to enhance depth of field of the eye, and/or to reduce the impact of off-axis stray light rays in creating halos and other visual artifacts may be considered special cases of the spatial modulation of light entering the cornea. It has been found that additional visual benefits may achieved by using other types of modulators. For example, it may be desirable to define other properties of an aperture in addition to the size and shape to provide a desired visual effect, such as for a given set of visual tasks. One way of doing so involves the use of an apodization mask to alter the phase and/or amplitude of light entering the eye.

In configurations in which electrodes 225, 2225 are a plurality of individually addressable electrodes arranged in a grid, the individual pixels may be selectively activated or deactivated. For example, such a configuration may allow for relocation of the geometric center of the aperture 260 and annulus 270 relative to the geometric center of the substrates or the eye's pupil.

The devices illustrated in FIGS. 2A, 2B, and 3-7 also may include an apodization mask as described with reference to FIGS. 2C and 2D, which may be static or dynamic. In some configurations, the structure described with respect to FIGS. 2C-2D may provided in addition to the other structures described. For example, the devices may include an additional layer, such as of a transparent polymer, that incorporates a refractive index gradient, or it may include an additional electroactive element 2200 in addition to the other elements described, or incorporated with the other elements as would be understood by one of skill in the art. As another example, the devices may include an layer that has an alterable index of refraction when electrically activated, or a layer incorporating a liquid crystal that alters its refractive index upon electrical activation. An apodization mask also may be provided by one or more of the layers described with respect to FIGS. 2-7. For example, a substrate 210, 520 may provide a static or dynamic mask, such as by including a refractive index gradient or a layer having an alterable index of refraction.

Phase amplitude variation may be introduced by using a refractive index gradient across the pupillary aperture that causes a variation in the optical path difference without affecting the level of defocus α. There are several parameters that may be varied across the pupillary aperture of an apodization mask as a function of the pupil radius r: the refractive index of the medium, the thickness of the material, the optical transmission, and the edge geometry (e.g., single or double, depending on whether the mask is circular or annular). The mask may be static or dynamic. A dynamic mask is adjustable by application of an externally applied force such as an electric potential.

A dynamic mask may be superior to a static mask in that as the target distance and illumination conditions change, the optics of the eye changes to adapt these changes in the environment. For example, the aberrations and depth of focus of an accommodated eye (or partially accommodated eye, for a presbyope) viewing a near object (target distance about 40 cm) are different for those of the same eye in its unaccommodated state, when viewing an object at 20 feet or greater. In particular the depth of focus available to the eye will depend on the type of vision correction provided to the patient, and therefore the design of the dynamic mask will complement the type and power of the vision correction device that the patient is already wearing, or is going to receive in addition to the mask. A preferred method of fabricating a dynamic mask may involve the use of a transparent liquid crystal layer hermetically encapsulated between two transparent sheets of flexible acrylic polymers, synthesized to be biocompatible in an ocular environment. Orientation of the liquid crystal layer by application of an electric field changes its refractive index. The modulation of optical transmission in a dynamic mask may be preferably provided by using a guest-host liquid crystal system, in which an electrochromic dye is incorporated into a transparent liquid crystal.

To diagnose and fit a patient with a dynamic mask, two measurements may be performed: a measurement of the size of the natural pupil as a function of ambient light level, and a measurement of the emerging wavefront of the eye fitted with the mask. A phase and amplitude profile of the mask suited to provide a desired retinal image quality (possibly excepting defocus) may be generated for distance vision over a range of ambient light levels. For example, the spatial frequency of a peak in the OTF of the combined eye and dynamic aperture system may be matched to the peak of the NCSF of the patient. The dynamic mask may be programmed to provide the appropriate correction based on the phase/amplitude profile when performing the intended visual tasks. For example, the mask may be entirely or partially inactive in bright outdoor light or other situations in which the natural pupil closes, which could reduce the effectiveness of the mask. In case of a mask encapsulated in an IOO, IOL, corneal inlay or corneal onlay, the dynamic mask may be implanted prior to performing the appropriate measurements and/or generating the phase/amplitude profile for the treated eye.

An electro-active element may be capable of switching between a first optical power and a second optical power. The electro-active element may have the first optical power in a deactivated state and may have the second optical power in an activated state. The electro-active element may be in a deactivated state when one or more voltages applied to the electrodes of the electro-active element are below a first predetermined threshold. The electro-active element may be in an activated state when one or more voltages applied to the electrodes of the electro-active element are above a second predetermined threshold. Alternatively, the electro-active element may be capable of "tuning" its optical power such that the electro-active element is capable of providing a continuous, or substantially continuous, optical power change between the first optical power and the second optical power.

Electro-active lenses may be used to correct for conventional or non-conventional errors of the eye. The correction may be created by the electro-active element, by the optical substrate or the ophthalmic lens, or by a combination of the two.

One or more electro-active elements having a dynamic aperture and/or a dynamic mask may be attached to or embedded within an optical perform, optic, or substrate that does not refract or diffract light for the purposes of correcting vision errors of the eye and thus does not provide focusing power. The electro-active element may be attached to or embedded within an ophthalmic lens that corrects for the user's refractive error caused by natural anatomical conditions and/or caused by the removal of a cataract or healthy crystalline lens. The ophthalmic lens may also correct any or all of the user's conventional and/or non-conventional errors of the eye. Thus, a dynamic aperture and/or dynamic mask may be integral with a focusing lens. Alternatively, an electro-active lens may have a first electro-active element having a dynamic aperture or dynamic mask. The first electro-active element or a second electro-active element in optical communication with the first electro-active element may be capable of correcting any or all of the user's conventional and/or non-conventional errors of the eye. The above devices may be a corneal onlay, a corneal inlay, an IOO, or an IOL, and may be used in optical communication with a focusing lens such as, by way of example only, an IOL, a crystalline lens, a corneal inlay, a corneal onlay, or a spectacle lens. The focusing lens may be static (incapable of altering its optical power) or dynamic (capable of altering its optical power).

Figure 7A:
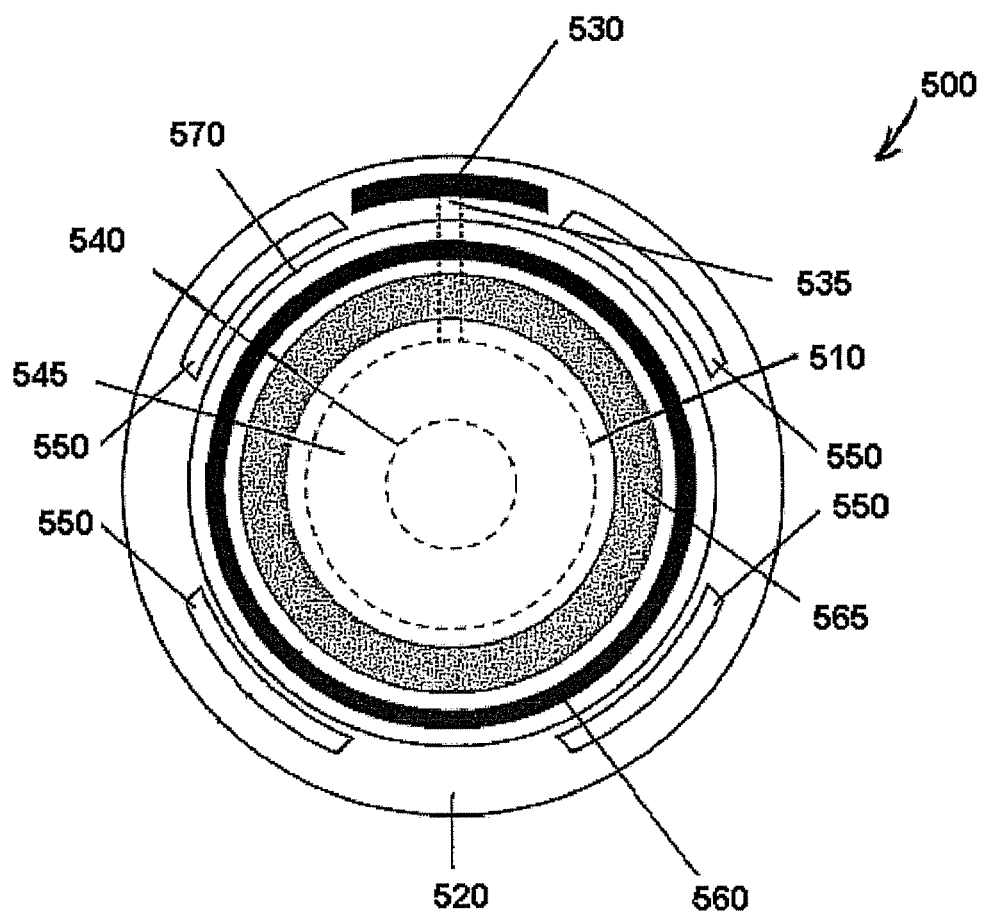
FIGS. 7A, 7B, and 7C show devices having a dynamic aperture which are useful as a corneal inlay, or corneal onlay.
Figure 7B:
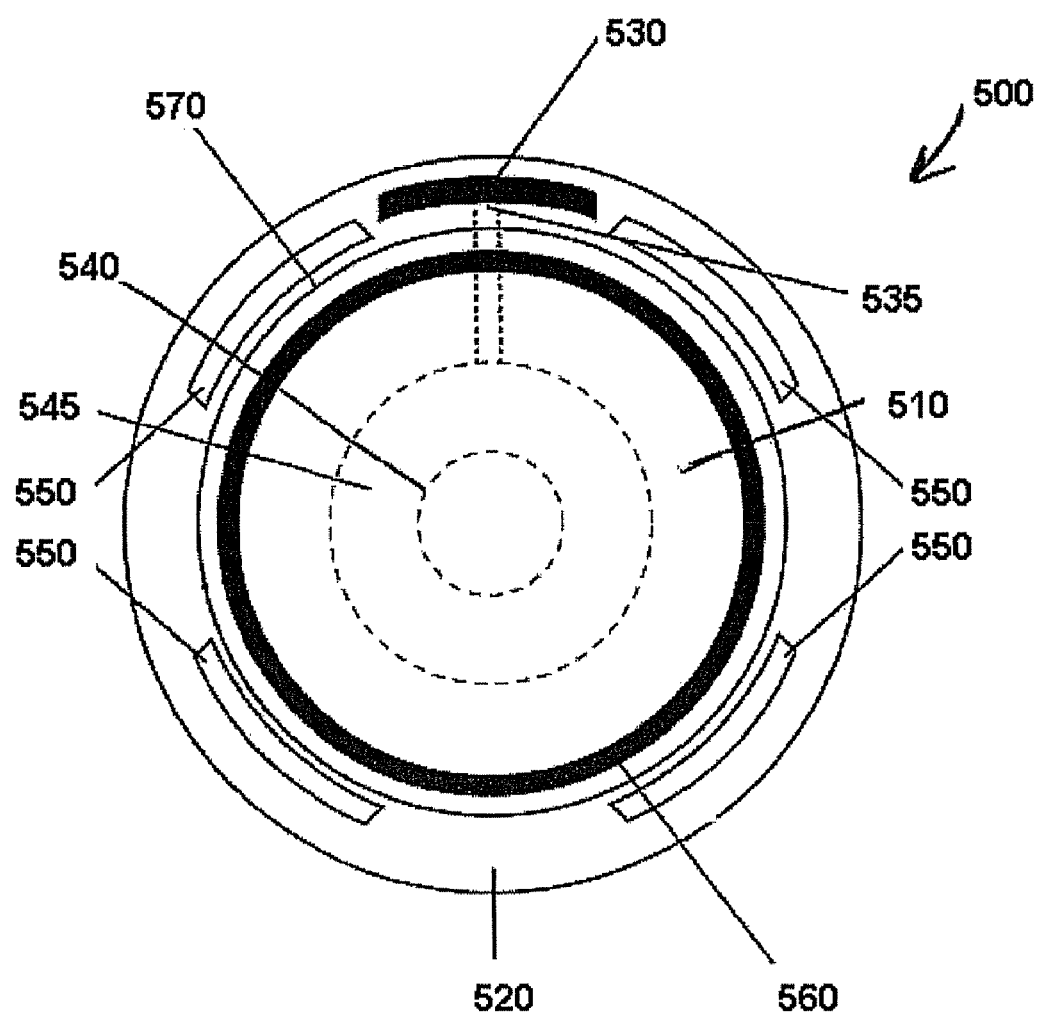
Figure 7C:
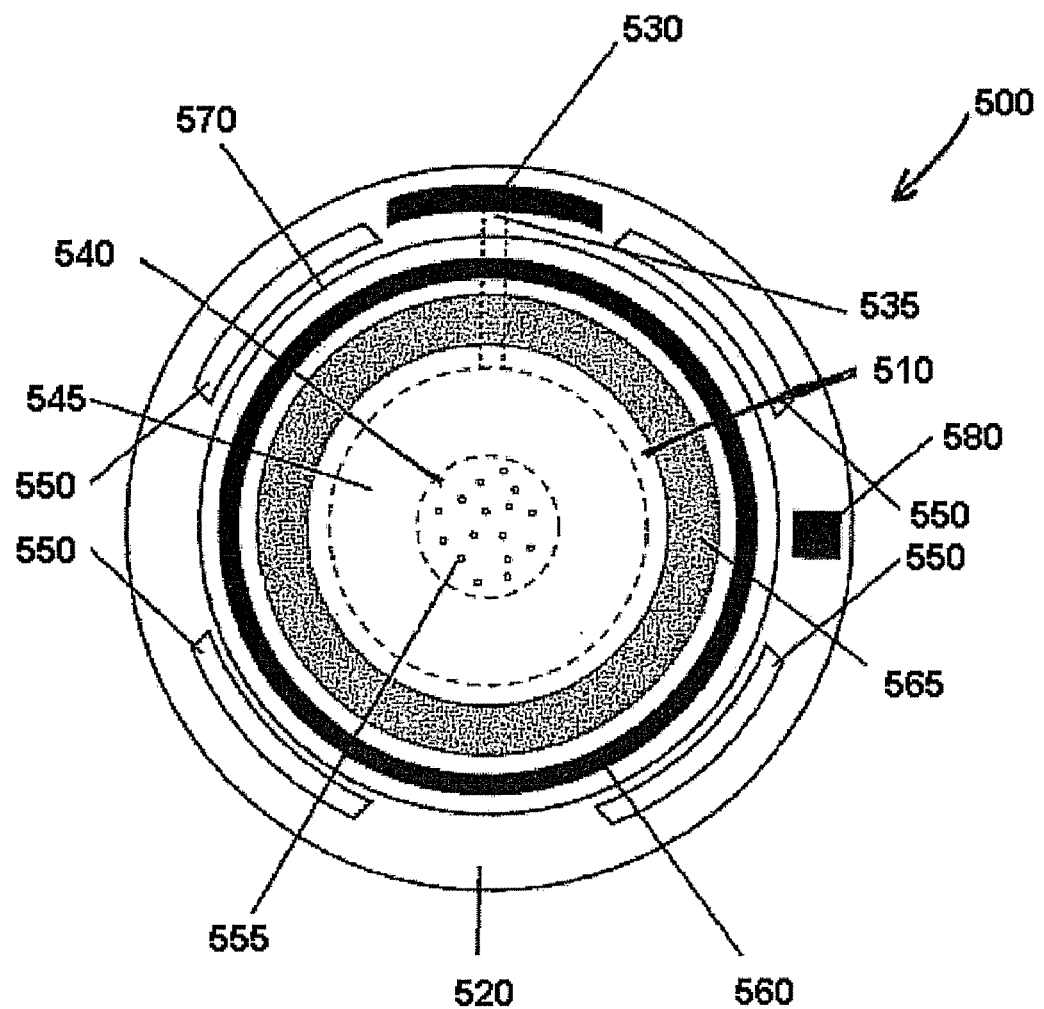

FIGS. 7A, 7B, and 7C show optical devices having a dynamic aperture which are useful as a corneal inlay, or corneal onlay. The devices shown in FIGS. 7A, 7B, and 7C may be modified slightly, for example by adding stabilizing haptics, for use as an anterior or posterior chamber IOO or IOL having a dynamic aperture. Optic or lens 500 may have one or more electro-active elements 510. Electro-active element 510 may be similar to electro-active elements 200 or 400 or may not have a dynamic aperture and/or apodization mask and may instead provide a changeable optical power. The electro-active element may be embedded within or attached to substrates 520. The substrates may have no optical power or may have one or more optical powers. The substrates and/or the electro-active elements may be capable of correcting for at least a portion of any or all conventional and/or non-conventional error of the eye. A controller 530 may be electrically connected to the electrodes in the electro-active elements by electrical connections 535. The electrodes may define a mostly transparent aperture 540 and a mostly opaque annulus 545. The term "mostly transparent" means approximately 50% or more optical transmission (and preferably 75% or more) and isn't meant to necessarily mean 100% optical transmission. The term "mostly opaque" means approximately 50% or less optical transmission (and preferably 35% or less) and isn't meant to necessarily mean 0% optical transmission.

The substrates may have one or more openings 550 and/or pores 555 to allow nutrients and/or cellular waste products to pass through the substrates and/or the electro-active elements. The openings and/or pores may be created, by way of example only, by a laser, or they may be machined or stamped. Typically, the openings and pores are located at non-electrical or otherwise non-critical areas of the lens or optic such as within a central region where the electrodes do not extend or apply power. These features are especially important when the lens or optic having a dynamic aperture is used as a corneal inlay or corneal onlay.

The controller may draw at least some of its electrical power from a power supply 560. The power supply may be attached and integral with the substrates or attached but not integral with the substrates. The power supply may be a thin film rechargeable battery such as those manufactured by Excellatron. The thin film rechargeable battery may be capable of being cycled in excess of 45,000 cycles. This may provide a usable lifetime of 20-25 years in the lens or optic. Two thin film rechargeable batteries may be used and may stacked one atop the other. In this configuration, one of the batteries may be used for 20-25 years and the other battery may be switched to when the first battery is no longer operable. Alternatively, the other battery may be switched to by a signal sent remotely to the controller. This may extend the lifetime of the optic or lens to 40-50 years. The power supply may also be a capacitor. The power supply may be remotely charged, by way of example only, by induction.

A light-sensitive cell 565 and piezo-electric materials may also be used to supplement and or augment the power supply's electrical power. Alternatively, the light sensitive cell and/or the piezoelectric materials may obviate the need for a power supply. The light-sensitive cell may be a solar cell. Alternatively, the light-sensitive cell may be a 1.5 µm photovoltaic cell. The photovoltaic cell is utilized and located out of the line of sight of the user and more preferably utilized and located peripheral to the margin of the pupil when partially dilated by darkness, but not fully dilated. The lens or optic may thus be charged by using an eye safe laser capable of energizing the 1.5 µm photovoltaic cell or cells. The user may position his or her chin and forehead into a device that provides the eye safe laser energy needed to energize the 1.5 µm photovoltaic cell or cells. This may be accomplished at home once a day or as needed. The proper energy can be provided through a normally dilated pupil or a fully non-medicated dilated pupil caused by a very dark room or by the device blocking out any ambient visible light. When utilizing a 1.5 µm photovoltaic cell or cells within the lens or optic, the cell or cells in may need to be capable of bending. When using a 1.5 µm photo-voltaic cell not capable of bending, multiple cells are used and are placed in a pattern that allows for folding or rolling the lens or optic over or around the cells prior to insertion into the eye.

The light-sensitive cell 565 may be a solar cell. The solar cell may be located in front of (closer to the cornea of the eye) and separately disposed from a portion of the iris of a user's eye. Thin electrical wiring may operably connect the solar cell to the controller of the optic or lens. The electrical wiring may pass through the pupil without touching the iris and operably connect to the IOO or IOL in the anterior or posterior chamber of the eye. The solar cell may be large enough such that it supplies enough electrical power to obviate the need for a separate power supply. The thin electrical wiring may not conduct electricity and may have a form factor which has the appropriate tensile strength to hold the solar cell in place. In some configurations, one or more small holes may be made in the iris by an ophthalmic laser such that the thin electrical wiring connects the solar cell to the IOO or IOL that houses an electro-active element.

A lens or optic as described herein may include a memory metal material 570 for re-establishing the proper shape, positioning and alignment of the device after being folded and inserted into an eye. A memory metal "remembers" its shape and attempts to regain its original geometry after being deformed (for example, while being folded in preparation for insertion into the eye). The memory metal may also function as an antenna for inductively charging the lens or optic or for receiving signals from a transmitter. The transmitter may send a signal to the lens or optic to change the diameter of the dynamic aperture or to change the lens's optical power.

A sensor 580 may be included. The sensor may be a range finder for detecting a distance to which a user is trying to focus. The sensor may be light-sensitive cell 565 for detecting light that is ambient and/or incident to the lens or optic. The sensor may include, for example, one or more of the following devices: a photo-detector, a photovoltaic or UV sensitive photo cell, a tilt switch, a light sensor, a passive range-finding device, a time-of-flight range finding device, an eye tracker, a view detector which detects where a user may be viewing, an accelerometer, a proximity switch, a physical switch, a manual override control, a capacitive switch which switches when a user touches the nose bridge of a pair of spectacles, a pupil diameter detector, a bio-feed back device connected to an ocular muscle or nerve, or the like. The sensor may also include one or more micro electro mechanical system (MEMS) gyroscopes adapted for detecting a tilt of the user's head or encyclorotation of the user's eye.

Figure 18:
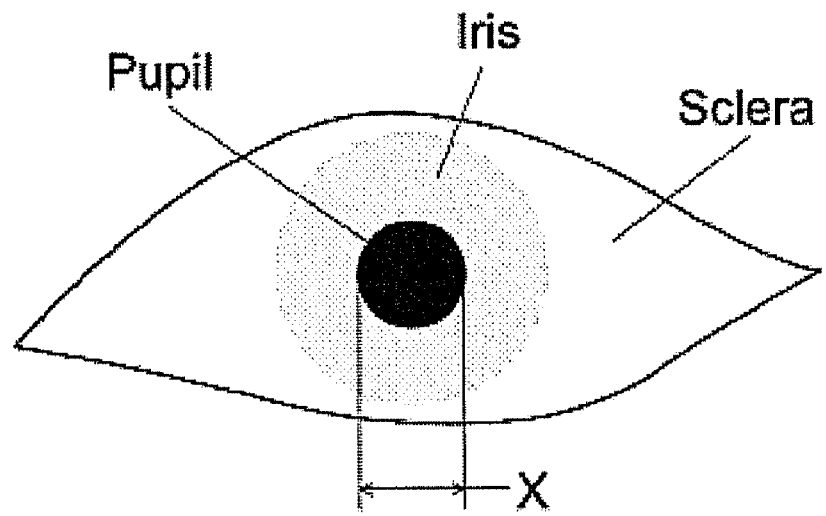
FIG. 18 shows that during the day, or in light, when a user's pupil is constricted, a sensor senses the increase of light and a controller may cause a dynamic aperture in an electro-active element to constrict.
Figure 18:
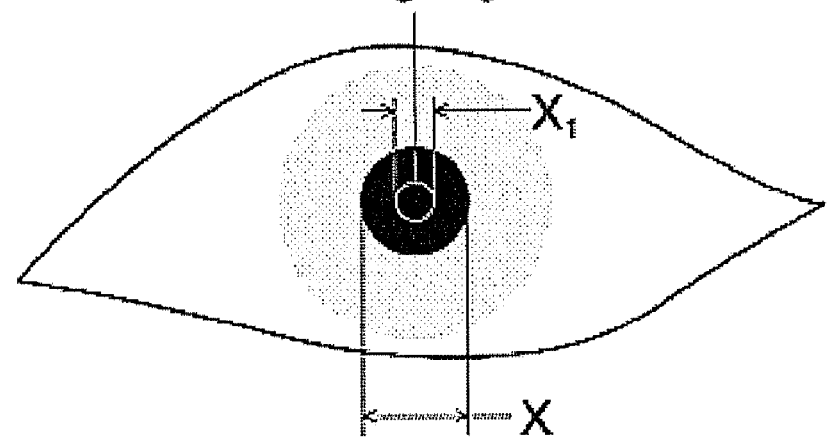
Figure 19:
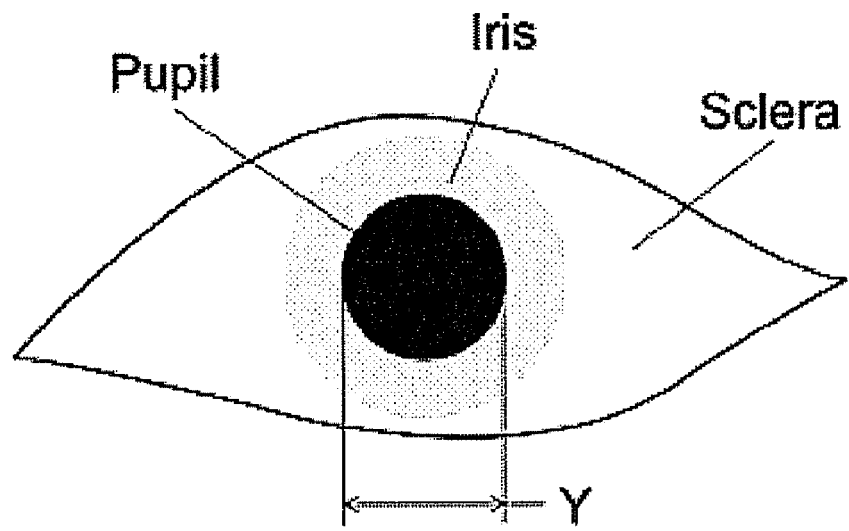
FIG. 19 shows that at night, or in darkness, when a user's pupil is dilated, a sensor senses darkness and a controller may cause a dynamic aperture in an electro-active element to dilate or remain dilated.
Figure 19:
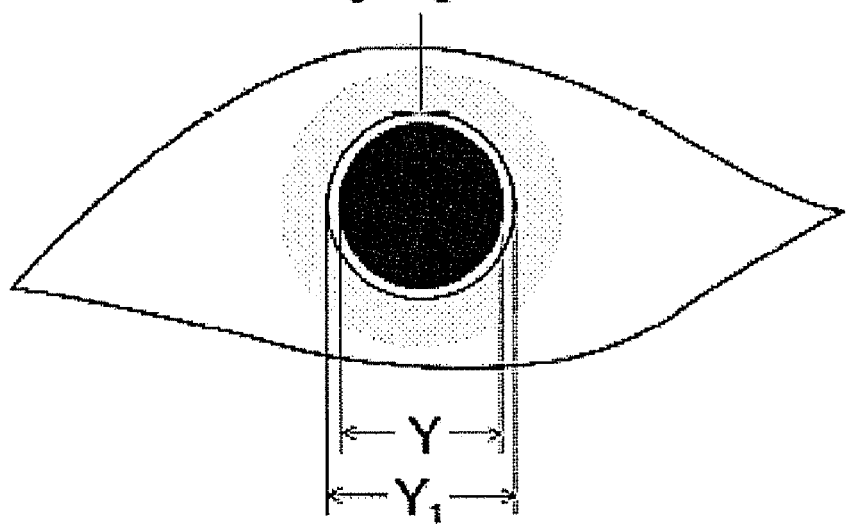

The sensor may be operably connected to the controller. The sensor may detect sensory information and send a signal to the controller which triggers the activation and/or deactivation of one or more dynamic components of the lens or optic. When a lens or optic includes an electro-active element having a dynamic aperture and/or apodization mask, the sensor, by way of example only, may detect the intensity of light and communicate this information to the controller. The sensor may be a photo-detector and may be located in a peripheral region of the lens or optic and located behind the iris. This location may be useful for sensing increases and/or decreases in available light caused by the constriction and dilation of the user's pupil. FIG. 19 shows that at night, or in darkness, when the user's pupil is dilated, the sensor senses darkness and the controller may cause the dynamic aperture to dilate or remain dilated. FIG. 18 shows that during the day, or in light, when the user's pupil is constricted, the sensor senses the increase of light and the controller may cause the dynamic aperture to constrict. A dynamic aperture may remain constricted until the sensor senses darkness or the lack of available light below a certain threshold in which case the controller may cause the dynamic aperture to dilate. The sensor may be located in any region of the lens or optic that works in an optimum manner. The controller may have a delay feature which ensure that a change in intensity of light is not temporary (i.e., lasts for more than the delay of the delay feature). Thus, when a user blinks his or her eyes, the size of the aperture will not be changed since the delay of the delay circuit is longer than the time it takes to blink. The delay may be longer than approximately 0.0 seconds, and preferably 1.0 seconds or longer.

The sensor, by way of example only, may detect the distance to which one is focusing. If the sensor detects that a user is focusing within a near distance range, the controller may cause the dynamic aperture to constrict to produce an increased depth of field. If the sensor detects that the user is focusing beyond the near distance range, the controller may cause the dynamic aperture to dilate. The sensor may include two or more photo-detector arrays with a focusing lens placed over each array. Each focusing lens may have a focal length appropriate for a specific distance from the user's eye. For example, three photo-detector arrays may be used, the first one having a focusing lens that properly focuses for near distance, the second one having a focusing lens that properly focuses for intermediate distance, and the third one having a focusing lens that properly focuses for far distance. A sum of differences algorithm may be used to determine which array has the highest contrast ratio (and thus provides the best focus). The array with the highest contrast ratio may thus be used to determine the distance from a user to an object the user is focusing on.

Figure 20:
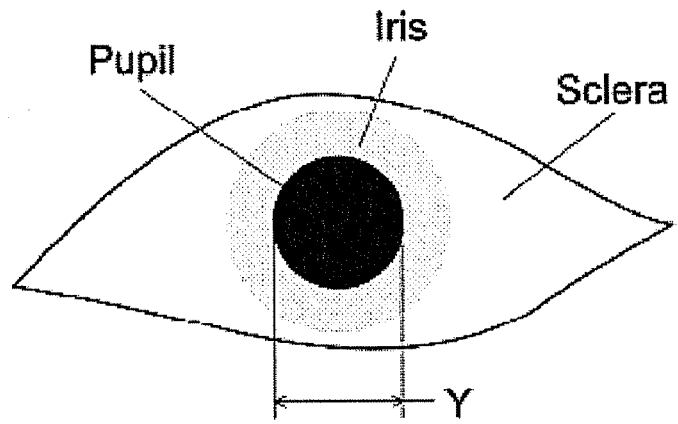
FIG. 20 shows the normal operation of a sensor and controller that have been overridden in which a dynamic aperture in an electro-active element is constricted for near distance tasks in dark lighting conditions even though a user's pupil is dilated.
Figure 20:
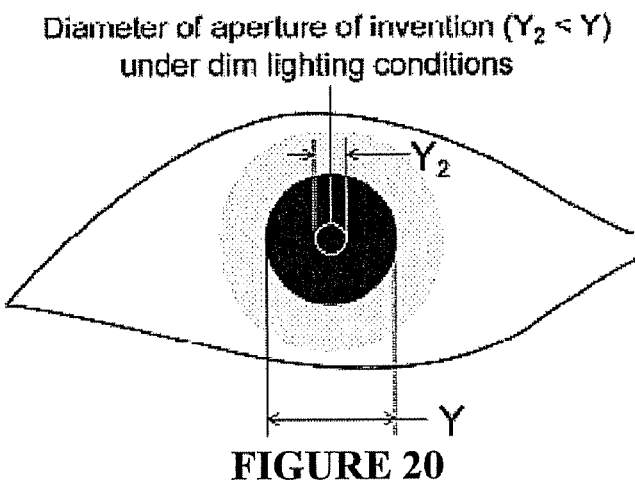

Some configurations may allow for the sensor and/or controller to be overridden by a manually operated remote switch. The remote switch may send a signal by means of wireless communication, acoustic communication, vibration communication, or light communication such as, by way of example only, infrared. By way of example only, should the sensor sense a dark room, such as a restaurant having dim lighting, the controller may cause the dynamic aperture to dilate to allow more light to reach the retina. However, this may impact the user's ability to perform near distance tasks, such as reading a menu. The user could remotely control the dynamic aperture of the lens or optic to constrict the aperture to increase the depth of field and enhance the user's ability to read the menu. FIG. 20 shows the normal operation of a sensor and controller that have been overridden in which a dynamic aperture is constricted for near distance tasks in dark lighting conditions even though the user's pupil is dilated. When the near distance task has completed, the user may remotely allow the sensor and controller to cause the aperture to dilate once again automatically thereby allowing the user to see best in the dim restaurant with regard to non-near distance tasks. When activated, the remote switch signal may be received, by way of example one, by the lens or optic via an antenna formed from the memory metal material 570.

The substrates described herein may be coated with materials that are biocompatible with anatomical objects in the eye. Biocompatible materials may include, for example, polyvinyldene fluoride or non-hydrogel microporous perflouroether. The substrates and the various electronics that are affixed to or embedded within the substrates may optionally be overcoated to be hermetically sealed to prevent or retard leaching. Additionally, the substrates may be designed to encapsulate the various electronics such that they are buried within the substrates.

Figure 21:
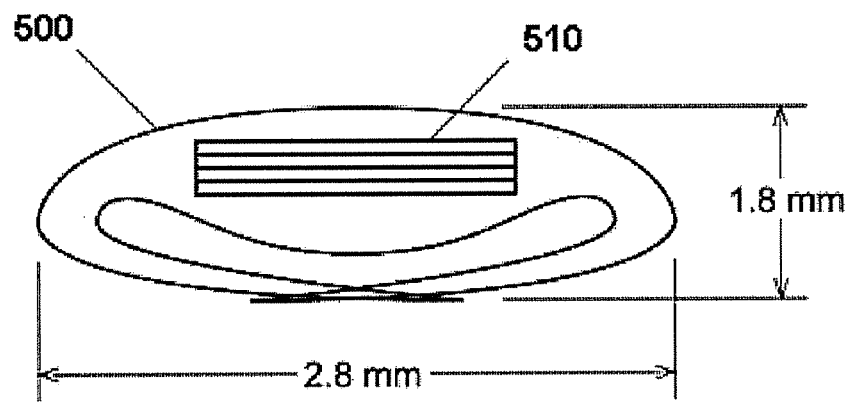
FIG. 21 shows a folded optic or lens having one or more electro-active elements.

The lenses and optics described herein may be bendable, foldable, and/or able to be rolled up for fitting during insertion through a small approximately 1 mm to 3 mm incision. A syringe-like device commonly used for implantation of IOLs having a piston may be used as an insertion tool that allows for a folded or rolled lens or optic to be placed properly where desired in either the anterior or posterior chamber of the eye. FIG. 21 shows a folded optic or lens having one or more electro-active elements.

Optical devices having a dynamic aperture and/or an apodization mask can be fit or implanted either monocularly (in only one eye of a user) or binocularly (in both eyes of a user). Because the dynamic aperture can be programmed to expand to a larger size at night or in dim lighting conditions when the pupil diameter of the user would naturally dilate, glare, halos, ghosting, and reduced light hitting the retina of the user are largely eliminated. In contrast to other IOLs, corneal onlays, and corneal inlays that do not have a dynamic aperture and are therefore sometimes fit for far distance correction in one eye and near distance correction in the other eye as a compromise due to glare, halos, ghosting, etc., the lenses and optics described herein allow for a binocular approach. It should be pointed out that the optics and lenses described herein can also be implanted or fit in monocular manner, if desired, and can be designed and fabricated in such a way that the central point of the dynamic aperture and/or mask may be remotely relocated relative to the center of the optic or lens after being implanted within or on the eye in order to better align the central axis of the dynamic aperture to the user's line of sight.

An optic or lens having a dynamic aperture and/or an apodization mask may be used in optical communication with a healthy but presbyopic crystalline lens, an underperforming or fully performing single focus IOL, static multifocal IOL, dynamic focusing IOL (such as that of an electro-active focusing IOL), or an accommodating IOL without a dynamic aperture, an eye having an iris that has been traumatized and is torn, has a hole, or does not contract or dilate properly, an iris devoid of pigment such as an iris of certain albinos, a fully performing or underperforming multifocal or single vision corneal inlay or corneal onlay without a dynamic aperture, a fully performing or underperforming multifocal or single vision spectacle lens without a dynamic aperture, or an eye that has had underperforming refractive surgery.

A "fully performing" lens is capable of properly focusing light on the retina. An "underperforming" lens is not capable of properly focusing light on the retina. In most cases, an optic or lens having a dynamic aperture and/or apodization mask will improve the quality of visual acuity as perceived by the user when used in association with and in optical communication with the various examples provided in the preceding paragraph. When used with a fully forming lens, a dynamic aperture increases the depth of field and acts to inhibit or remove some or most of the higher aberrations of a user's eye.

A lens or optic that houses an electro-active element as disclosed herein can be comprised of ophthalmic materials that are well known in the art and used for IOLs, or corneal inlays. The materials can be flexible or non-flexible. For example, an IOO may be made from two approximately 100 μm layers of, for example, a polyether, a polyimide, a polyetherimide, or a polysulphone material having the appropriate electrodes, liquid crystalline material (which may be doped with a dichroic dye), optional polarizing layers, power supply, controller, sensor and other needed electronics. Each 100 μm layer is used to form a flexible envelope that sandwiches and houses the electronics and electro-active material. The total thickness of the working optic is approximately 500 μm or less. The outer diameter of is approximately 9.0 mm (not including any haptics). The IOO may be capable of being folded and inserted into the eye through a small surgical incision of approximately 2 mm or less. In some configurations, a thin layer of memory metal is utilized as part of the IOO to aid in opening the IOO to its proper shape and location after it has been inserted into the eye's anterior or posterior chamber.

A tint or a filter may be incorporated into a lens or optic to filter high energy blue light and/or ultra-violet light. The filter or tint may also be used to enhance contrast sensitivity as perceived by the user.

The diameter of the IOO or IOL may be between approximately 5 mm and approximately 10 mm (not including haptics), depending upon the lens's or optic's intended application. Other dimensions are possible as well When used as a corneal inlay, the diameter of an optic or lens having a dynamic aperture and/or apodization mask must be less than the diameter of the cornea. In some configurations, the optic or lens can have a diameter between approximately 5 mm and approximately 14 mm. The outer surface of the substrates may be curved to substantially match the curvature of the cornea, such as when used in a corneal inlay, or to match any other desired curvature, or the outer surface of substrates may be planar.

Figure 8:
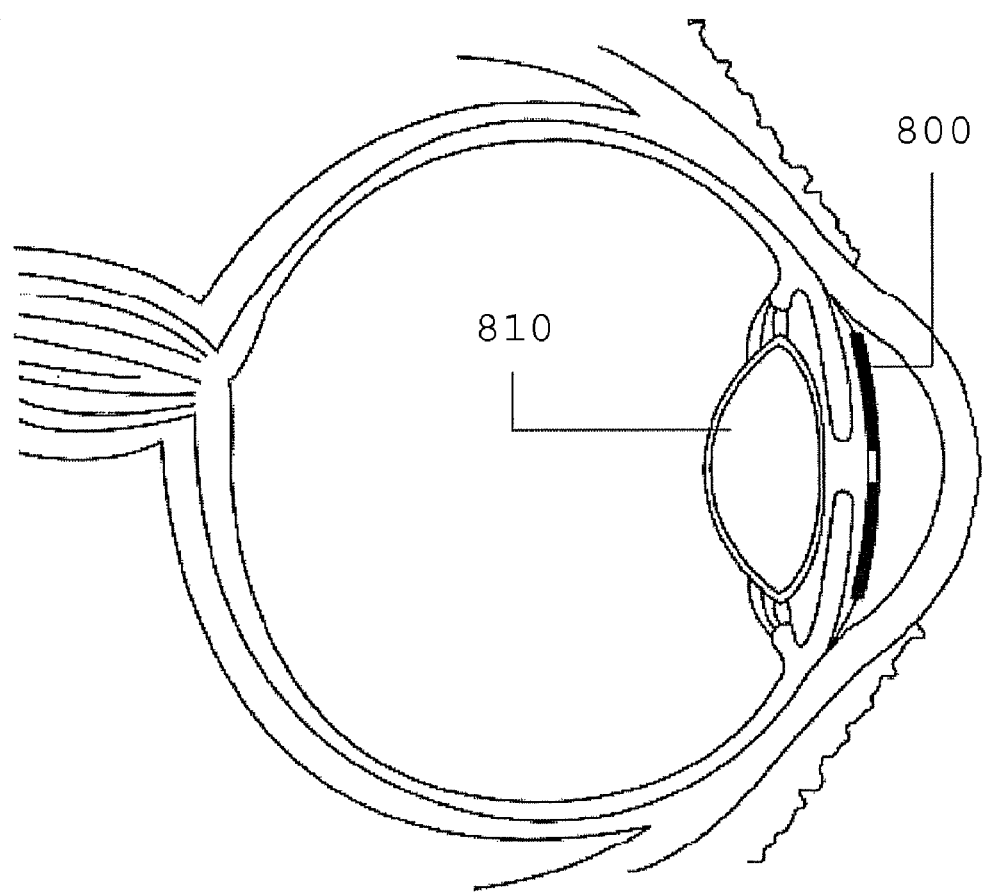
FIG. 8 shows an IOO located in an anterior chamber of an eye and in optical communication with a healthy presbyopic crystalline lens.
Figure 9:
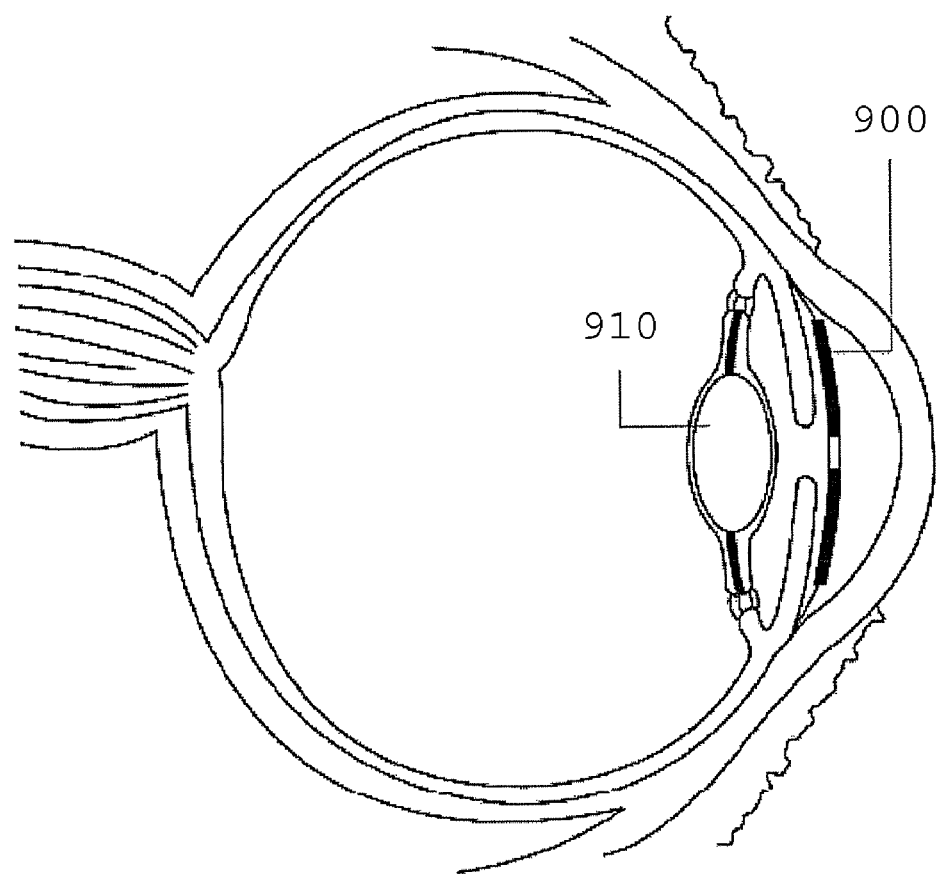
FIG. 9 shows an IOO located in an anterior chamber of an eye and ill optical communication with an IOL.
Figure 10:
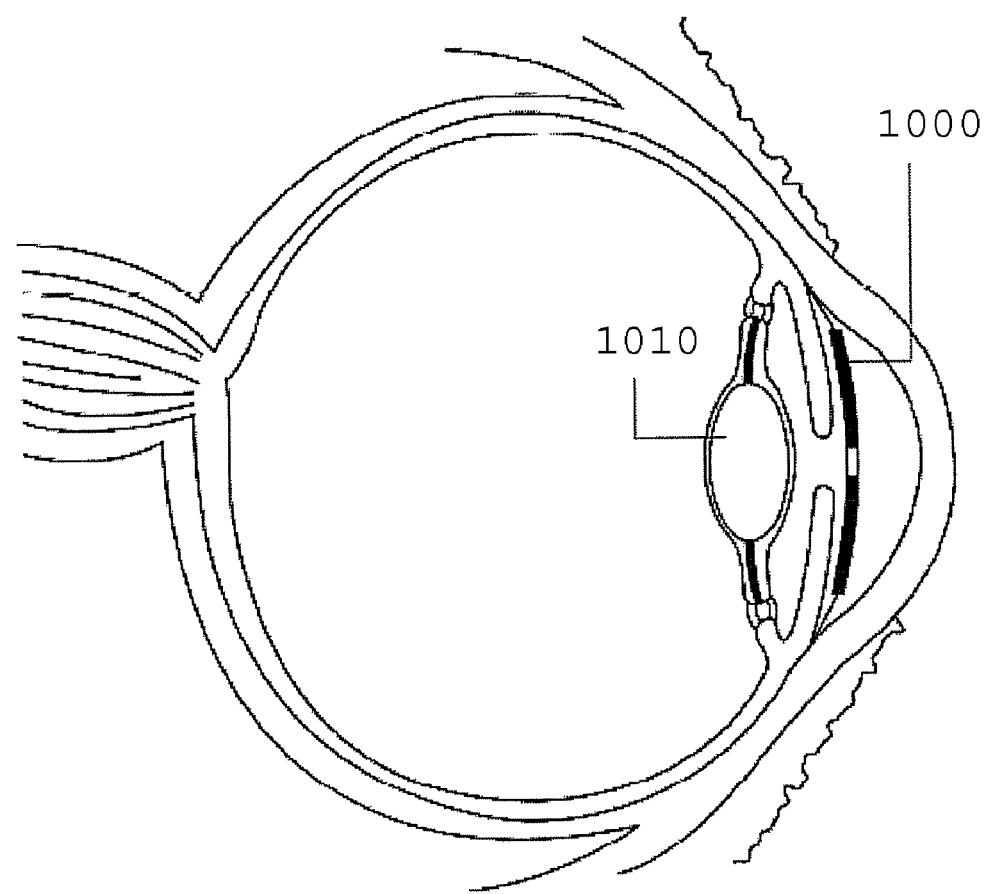
FIG. 10 shows an IOO located in an anterior chamber of an eye and in optical communication with an IOL that corrects for far distance vision only.
Figure 11:
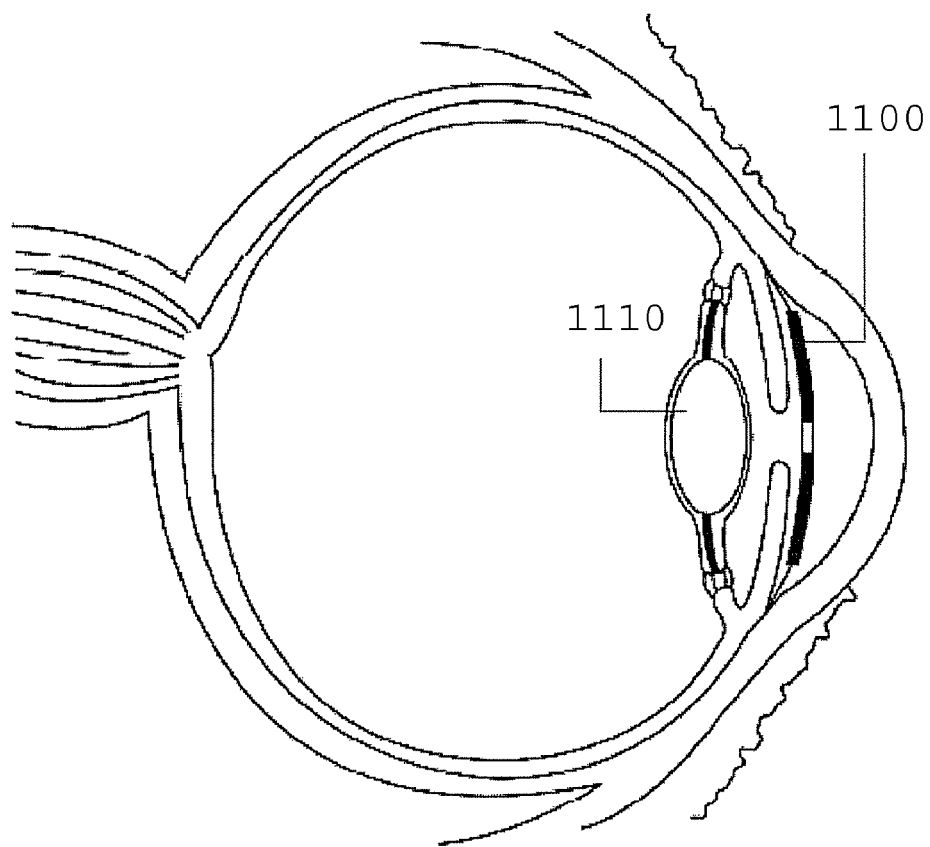
FIG. 11 shows an IOO located in an anterior chamber of an eye and in optical communication with an IOL that corrects for far distance vision and near distance vision.
Figure 12:
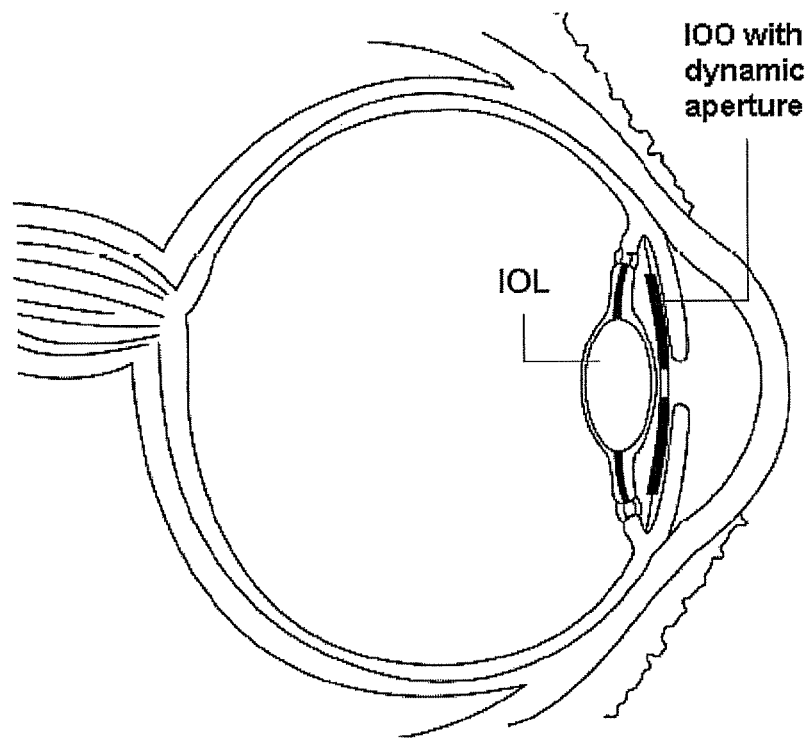
FIG. 12 shows an IOO located ill a posterior chamber of an eye and ill optical communication with an IOL.
Figure 13:
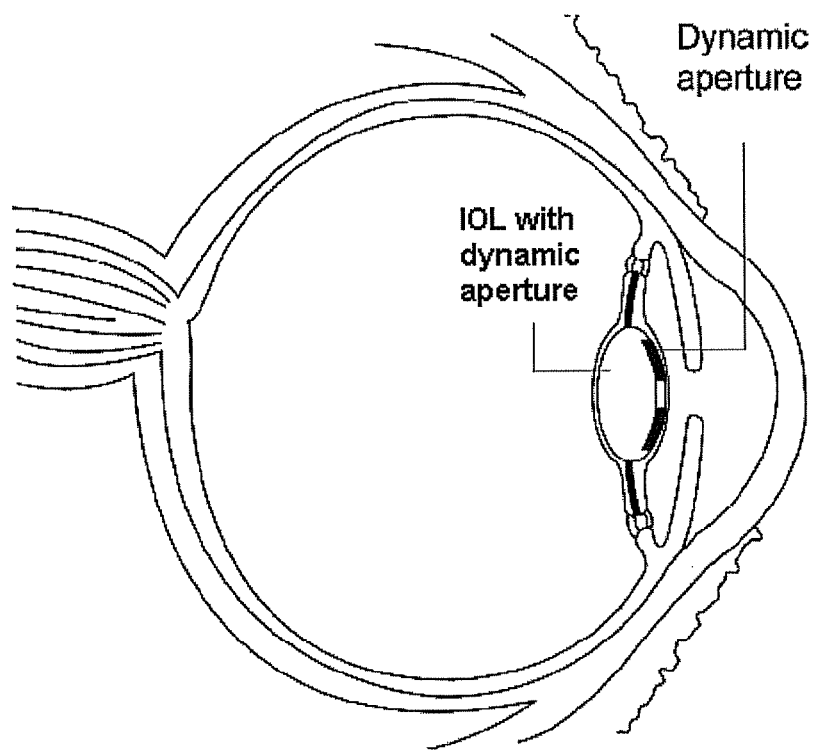
FIG. 13 shows an IOL having a dynamic aperture in the portion of the IOL closest to the eye's pupil.
Figure 14:
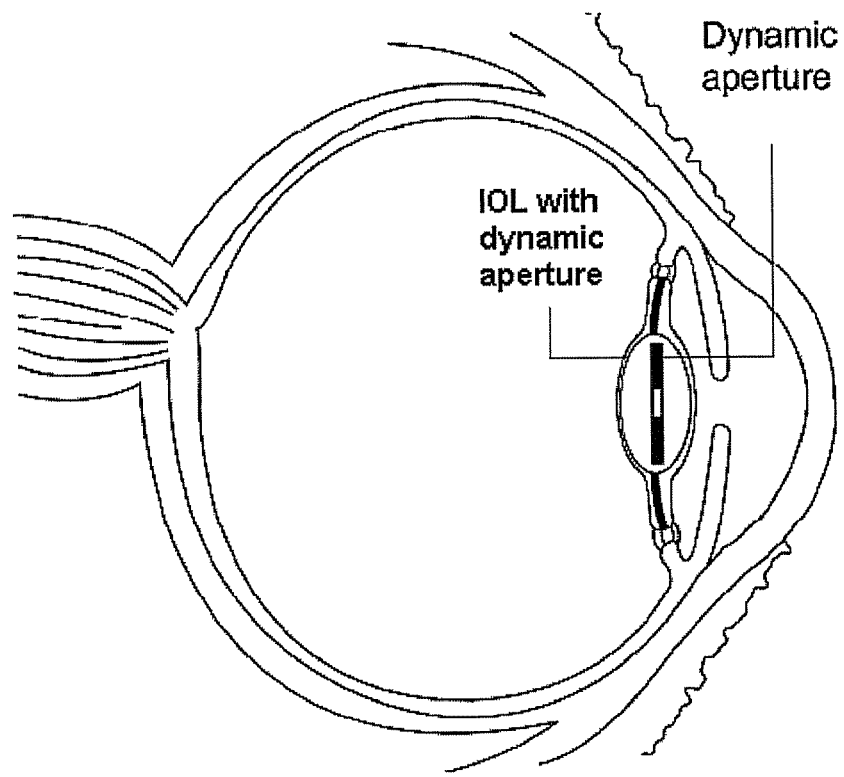
FIG. 14 shows an IOL having a dynamic aperture in the middle portion of the IOL.
Figure 15:
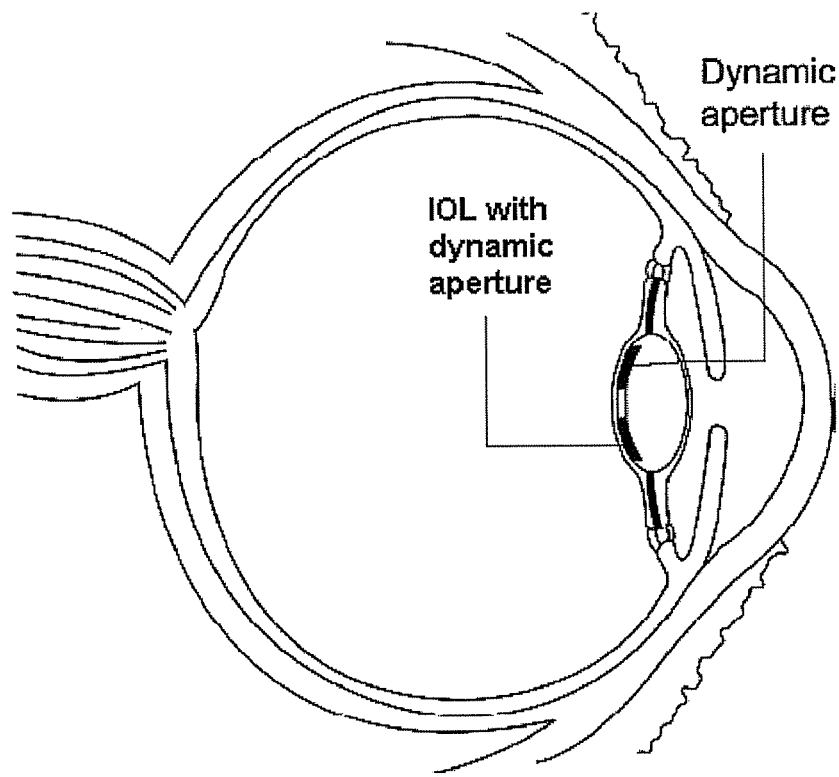
FIG. 15 shows an IOL having a dynamic aperture in the portion of the IOL closest to the eye's retina.
Figure 16:
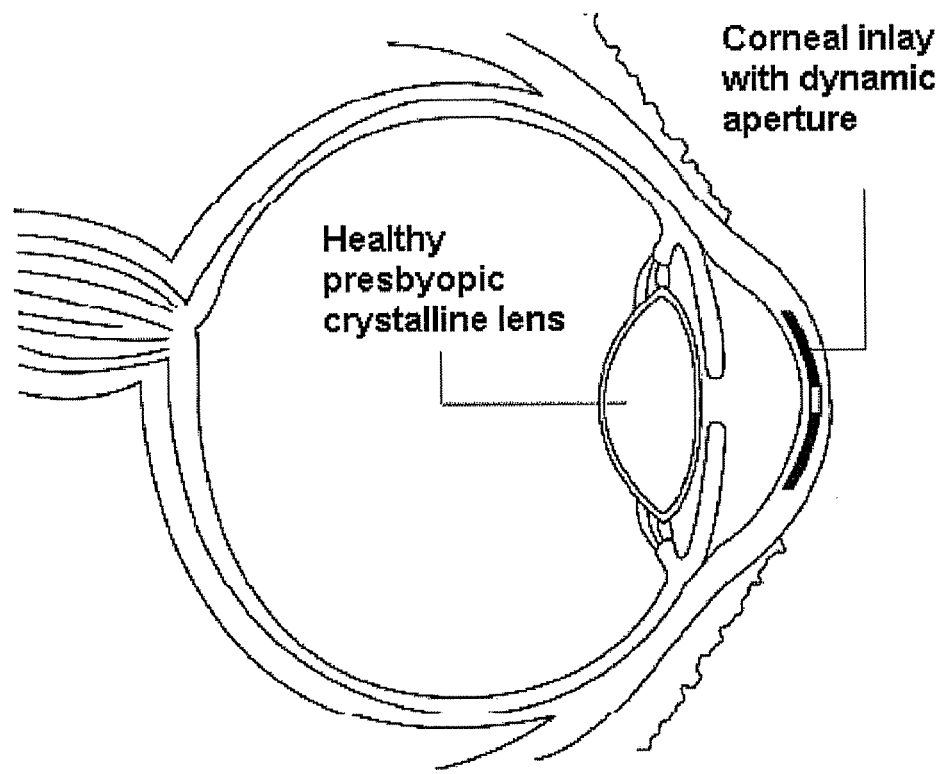
FIG. 16 shows a corneal inlay having a dynamic aperture in optical communication with a healthy presbyopic crystalline lens.
Figure 17:
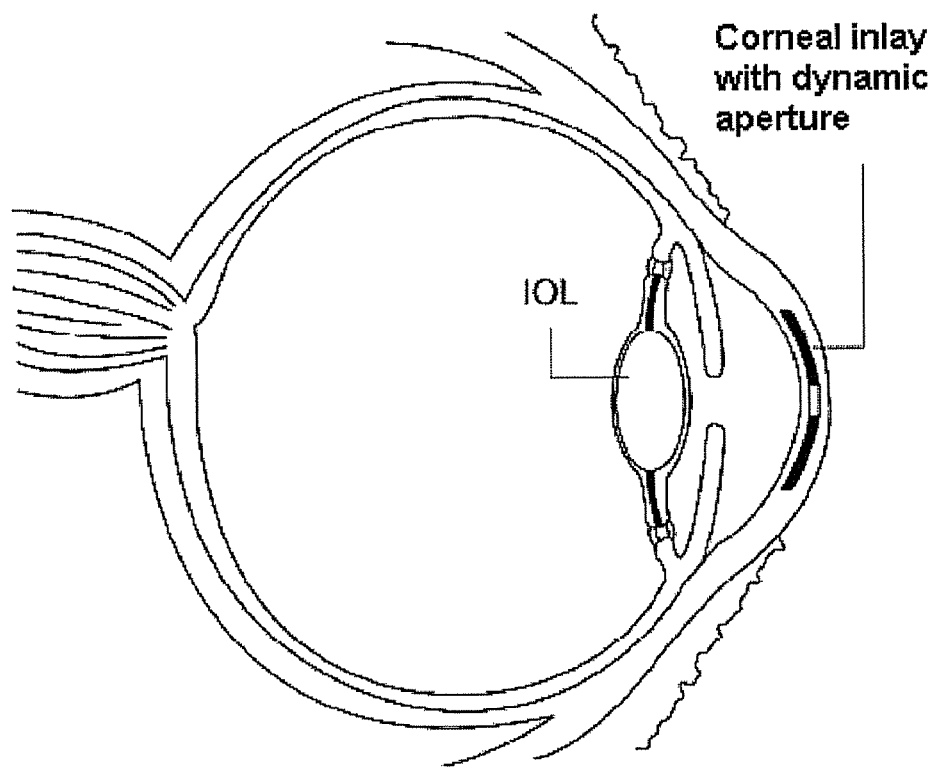
FIG. 17 shows a corneal inlay having a dynamic aperture in optical communication with an IOL.

FIG. 8 shows an IOO 800 located in an anterior chamber of an eye and in optical communication with a healthy presbyopic crystalline lens 810. The IOO may include a dynamic aperture, a dynamic mask, or both. In configurations including a dynamic aperture, the IOO may provide for improved intermediate and near vision by increasing the depth of focus. FIG. 9 shows an IOO 900 located in an anterior chamber of an eye and in optical communication with a far and near vision IOL 910. The IOO may include a dynamic aperture, a dynamic mask, or both. An IOO including a dynamic aperture may provide for increased depth of focus. FIG. 10 shows an IOO 1000 located in an anterior chamber of an eye and in optical communication with an IOL 1010 that corrects for far distance vision only. The IOO may include a dynamic aperture, a dynamic mask, or both. The configuration shown in FIG. 10 may be useful for providing an increased depth of field for providing near distance and/or intermediate distance correction by way of a dynamic aperture. FIG. 11 shows an IOO 1100 located in an anterior chamber of an eye and in optical communication with an IOL 1110 that corrects for far distance vision and near distance vision. The IOO may include a dynamic aperture, a dynamic mask, or both. A dynamic aperture may be useful for providing an increased depth of field for providing intermediate distance correction. FIG. 12 shows an IOO 11200 ocated in a posterior chamber of an eye and in optical communication with an IOL. The IOO may include a dynamic aperture, a dynamic mask, or both. FIG. 13 shows an IOL 1310 having a dynamic aperture in the portion of the IOL closest to the eye's pupil. The IOL also may include a dynamic mask. FIG. 14 shows an IOL having a dynamic aperture in the middle portion of the IOL. The IOL also may include a dynamic mask. FIG. 15 shows an IOL having a dynamic aperture in the portion of the IOL closest to the eye's retina. The IOL also may include a dynamic mask. FIG. 16 shows a corneal inlay in optical communication with a healthy presbyopic crystalline lens. The inlay may include a dynamic aperture, a dynamic mask, or both. FIG. 17 shows a corneal inlay in optical communication with an IOL. The inlay may include a dynamic aperture, a dynamic mask, or both. It should be noted, that it is not possible to show all possible configurations, embodiments, combinations, and placements of the present invention. For example, a corneal inlay having a dynamic aperture are not shown. In addition, a static or dynamic apodization mask may be incorporated into an IOO, IOL, corneal only, coneal inlay, or other device as shown and described, with or without a dynamic aperture. However, these will be apparent to those skilled in the art.

An IOO or IOL including a dynamic aperture and/or an apodization mask can be surgically inserted during the initial surgical procedure that inserts a conventional IOL without a dynamic aperture. Alternatively, the IOO or IOL may be surgically inserted as a follow on surgical procedure hours, days, weeks, months, or years after the initial IOL surgery.

Successful operation of a lens or optic including a dynamic aperture is dependent upon obtaining the maximum allowable transmission through the mostly transparent aperture and the minimum allowable transmission through the mostly opaque annular region. Experiments were conducted with neutral density (ND) optical filters with ND values between 0 and 1.0 in which holes having a 1.5 mm diameter were formed in the filters to create apertures. In some experiments, a second filter was placed over the aperture to simulate the transmittance through the aperture. Neutral density is measure of light transmittance based on a logarithmic scale and is related to the transmission (T) via the following relationship:

$$T=10^{-ND} \quad \text{Equation 3}$$

In the experiment, the filter was held in front of and very close to the eye of a non-corrected +2.50 D presbyopic patient. The presbyopic patient looked at a near vision target at approximately 13 inches from the patient's eye through the aperture. It was discovered that such an aperture works for increasing depth of field by providing good visual acuity and contrast sensitivity, but only under certain conditions.

In general, the best results were obtained when the ND value of the mostly transparent aperture was less than approximately 0.1 (T greater than approximately 80%) and the difference in ND values between the mostly transparent aperture and the mostly opaque annulus was greater than approximately 0.3. In a preferred configuration, the ND value for the mostly transparent aperture may be less than approximately 0.04 (T greater than approximately 90%) and the ND of the mostly opaque annulus is greater than approximately 1.0 (T less than approximately 10%). While increasing the difference in ND values between the mostly transparent aperture and the mostly opaque annulus can compensate for a high ND value in the mostly transparent aperture, it will lead to an undesirable decrease in overall transmission of light to the retina.

The optical effects believed to result from use of an aperture and/or apodization mask will now be described. Retinal image quality can be quantitatively described by an optical transfer function (OTF) that is the plot of the value of the complex contrast sensitivity function as a function of the spatial frequency of the target object. A complex contrast sensitivity function can be used to characterize the image quality because the optics of the eye may change the spatial frequency of the image relative to that of the target, dependant on the target spatial frequency, in addition to reducing the contrast of the image. In principle, an OTF can be constructed for every object distance and illumination level. The OTF of the eye varies with object distance and illumination level, because both of these variables change the optics of the eye. The OTF of the eye may be reduced due to refractive errors of the eye, ocular aberrations or loss of accommodative ability due to onset of presbyopia.

The image of a point object is the Fourier transform of the aperture convoluted with the modulation transfer function (MTF) of the imaging optics, where the MTF is the real component of the OTF discussed above and shown in Equation 1. The resulting point image is known as the point spread function (PSF), and may serve as an index of measurement of the quality of the ocular optic (i.e., a bare eye or eye corrected with a vision care means). The PSF of the retinal image is found to correlate with the quality of visual experience, especially when it is compromised by halos or glint or other image artifacts. Thus, a systematic approach may be applied to designing an aperture by using a pupil apodization function. Such a function may be consistent with other previous representations of an aperture, such as that published by Guyon (Guyon, O, "Phase-induced amplitude apodization of Telescope Pupils in Extrasolar Terrestrial Planet Imaging", Astron & Astrophys, 401 (2003); pp 379) shown in Equation 1:

$$\Psi_O(x) = \Psi_E(x) - \Psi_E(x) \times \hat{M}(x) \quad \text{Equation 1}$$

In which $\Psi_O(x)$ and $\Psi_E(x)$ represent the complex amplitudes of the entrance and exit pupils, respectively, $\hat{M}(x)$ represents the Fourier transform of the mask shape, and x represents a convolution.

Similar formulations of apertures are described in, for example, Martinache F, "A Phase-Induced Zonal Zernicke Apodization Designed for Stellar Coronagraphy", in J Opt A., Pure Appl Opt, 6 (2004), pp 809-814. The apodization function may be used to introduce defocus as described in U.S. Pat. No. 5,980,040 by introducing an apodization function or an aperture that alters the amplitude of the wavefront as a function of the pupillary radius. It is also possible to introduce an artificial aperture that alters the phase of the wavefront as a function of pupillary radius, having a beneficial impact on the PSF. A quadratic phase distribution leaving the real amplitude of the apodization function unchanged can lead to defocus, e.g., $$\Psi_E(x) = \Pi(x) e^{-i\alpha x^2} \quad \text{Equation 2}$$

at the entrance pupil, with $\Pi(x)=1$, if $|x| \leq \frac{1}{2}$ and 0 otherwise, where $\alpha$ is a parameter representing the amount of defocus.

Therefore, to match the aperture to a given set of visual tasks, the geometry and optical properties of the aperture may be relative to a desired PSF for the set of visual tasks. To do so, the retinal image quality (for example, as defined by the PSF, or the OTF of the ocular system) may be matched to the visual perception experienced by an individual. Visual perception may be characterized by the neural contrast sensitivity function (NCSF). One step in the translation of a retinal image to a visual perception is the neuronal transfer of "visual information," i.e., the electrical signals produced by the retinal photoreceptors on receiving the image on the fovea. The neuronal transfer process is subject to noise, which can cause a degradation of image contrast in this case. The efficiency of neuronal transfer can be expressed as a function of a spatial frequency or a set of spatial frequencies of the retinal image, retinal illuminance, and the location of the point on the fovea with respect to the center of the exit pupil. Therefore, a maximum, optimum, or desirable aperture performance may be obtained by an aperture that can modulate the quality of the retinal image such that the OTF of the combined optical system, including the aperture, has a peak value of contrast at a spatial frequency that matches the peak of the NCSF of a particular individual. Although the chromaticity of the viewed image may affect the relationship between the NCSF and perceived quality, the present disclosure does not consider this factor, and provides an achromatic assessment of the retinal image quality and its match to the NCSF.

Different variables may be used to change the performance of an aperture. For example, U.S. Pat. Nos. 5,786,883 and 5,757,458 to Miller et al. describe the effects of an annular aperture, apertures that have multiple optical zones for different types of photoreceptors, and variations in aperture size. In general, the depth of focus increases and the retinal image quality improves as the aperture decreases in size. However, the total MTF of the combined eye and aperture system is degraded with increased aperture size. In general, the improvement of retinal image quality improves until the aperture size becomes about 2 mm or less. Below this point, the effects of diffraction may overcome the positive effect due to enhancement of the depth of field.

Two types of functional adjustments may be made within an aperture: the optical path difference caused by at a point within the aperture as a function of location (i.e., distance from the pupillary center and its azimuth), and its optical transmission. For a two dimensional aperture orthogonal to the optic axis of the eye, a description of the optical transmission is provided by a pupil apodization function, as shown in Equation 2 for $\alpha=1$. More generally, this is true for a two dimensional aperture in another plane, since the aperture may be projected onto a plane orthogonal to the optic axis of the eye. Clinical benefits of this approach have been reported in, for example, Applegate R A, et al, "Aberrations and Visual performance, Part I, Optical and neural Limits to Vision", Presented at the Wavefront Congress, 2005, which describes the MTF of the eye as a function of pupillary apertures. Application of an aperture enhances the low spatial frequency MTF at the expense of the high spatial frequency values of the MTF function of the eye. In effect, the aperture functions as a low band pass spatial frequency filter. Since the NCSF of a normal human eye typically peaks at 4-8 cycles/degree, this shift of MTF and associated OTF values of the retinal image enables the OTF to better match the NCSF of the eye. As previously mentioned, improving image quality at low spatial frequencies may enhance visual comfort and the subjective quality of vision.

The pupil apodization described by Guyon and others relates to enhancement of the resolution of a telescope system. Their assumption was that the emerging wavefront from the star was extremely flat, and in no need of correction. When designing for a human visual system, wavefront aberrations may be corrected at the expense of the OTF at high spatial frequencies. That is, a lower optical resolution may be acceptable to approach an OTF of the human visual system that is peaked at mid to low spatial frequencies, and a PSF that is diffraction limited at least for a few (1-3) Airy diameters ($\lambda/d$, when $\lambda$ is the wavelength of light, and d is the pupillary aperture).

Guyon also investigated the effect of the distance between the center of the aperture and the optic axis of the system on the PSF of the optical system, and showed that this parameter could be optimized to provide an optimum PSF without affecting the net optical transmission of the wavefront through the aperture. Also, the geometry of the inner edge of the aperture can further modulate the OTF of the entrance pupil, and thus enhance the OTF of the eye in low to mid spatial frequency region. Even patients with defocus or low order aberrations may benefit from a mask with specific edge geometries designed either individually for each, or for that particular type of vision error. For example, a patient with astigmatism may be fitted with a mask that will have an elliptical shape, with the minor axis of the ellipse matching the astigmatic axis of the patient. In this case, the depth of focus is increased preferentially along the direction of the astigmatic axis. Such a patient may be able to achieve optimum vision using a spherical correction. The geometry and optical transmission characteristics of the outer edge of the aperture (for an annular aperture) may be designed to minimize the effect of diffraction from this edge.

In Guyon and other astronomical work, phase amplitude variation across the pupillary aperture has been achieved by using mirrors (e.g., the PIAA technique, first proposed by Guyon and Doddier). While suitable for larger-scale applications such as telescopes, these design solutions cannot readily be adapted to clinical device such as those described herein.

To achieve some of the features and benefits described herein, it may be preferable to incorporate a dynamic aperture and/or apodization mask into a device that may be fixed relative to the pupil. Examples of such devices include IOOs, IOLs, corneal inlays, and corneal onlays. Otherwise the effects of the device may be reduced or eliminated, or the device may have an undesirable effect on the wearer's vision. Thus, some features described herein may be less desirable for incorporation into devices that do not remain fixed relative to the wearer's pupil, such as contact lenses and spectacle lenses.

While illustrative and presently preferred embodiments of the invention have been described in detail herein, it is to be understood that the inventive concepts may be otherwise variously embodied and employed, and that the appended claims are intended to be construed to include such variations, except as limited by the prior art.

What is claimed is:

1. An ophthalmic device comprising:
an apodization mask comprising an electro-active, transparent substrate;
wherein the substrate has at least one optical transmission property that is alterable by electrical activation.

2. The device of claim 1, wherein the device is capable of being surgically implanted in a user's eye.

3. The device of claim 1 wherein, when worn by a wearer, the substrate is fixed in position relative to the wearer's pupil.

4. The device of claim 1, further comprising a dynamic aperture.

5. The device of claim 4, wherein at least one the shape of the aperture and the size of the aperture is optimized according to a modulation transfer function of the wearer's eye.

6. The device of claim 4, wherein the geometry of the aperture is remotely adjustable.

7. The device of claim 1, wherein the at least one optical transmission property is at least one of the transmitted amplitude and the transmitted phase of light transmitted by the substrate.

8. The device of claim 7, wherein the apodization mask provides a phase and amplitude profile associated with a retinal image quality for distance vision at an ambient light level range.

9. The device of claim 1, wherein the at least one optical transmission property is the index of refraction of the substrate.

10. The device of claim 9, wherein the index of refraction of the substrate in the visual spectrum changes by at least 0.1 units upon electrical activation.

11. The device of claim 10, wherein the substrate comprises a liquid crystal layer, and the index of refraction of the substrate is alterable by electrical activation of the liquid crystal layer.

12. The device of claim 11, wherein the liquid crystal layer comprises a guest-host mixture.

13. The device of claim 11, wherein the liquid crystal layer is homogeneous.

14. The device of claim 11, wherein the liquid crystal layer is electrically addressable over an area of at least about 0.25 μm2 without affecting the response of adjacent material.

15. The device of claim 11, further comprising a computerized controller capable of activating multiple segments of the liquid crystal layer.

16. The device of claim 15, wherein the controller is embedded into the ophthalmic device.

17. The device of claim 15, wherein the controller is configured to activate segments in a pattern corresponding to a mask that modulates the amplitude, the phase or both the amplitude and the phase of light is transmitted through the device into the eye of a user fitted with the device.

18. An ophthalmic device, comprising:
an apodization mask comprising a transparent substrate;
wherein the substrate has at a refractive index gradient of at least 0.01 units/mm in at least one meridian.

19. The device of claim 18, wherein the refractive index gradient does not affect the level of defocus for light transmitted through the mask.

20. The device of claim 18 wherein, when the device is worn by a wearer, the substrate is fixed in position relative to the wearer's pupil.

21. The device of claim 18, further comprising a dynamic aperture.

22. The device of claim 21, wherein at least one the shape of the aperture and the size of the aperture is optimized according to a modulation transfer function of the wearer's eye.

23. The device of claim 21, wherein the geometry of the aperture is remotely adjustable.

24. An ophthalmic device comprising:
a substrate; and
a liquid crystal layer having a variable optical transmission of about 30%-99% upon electrical activation of the liquid crystal layer.

25. The device of claim 24, wherein the liquid crystal layer comprises a guest-host mixture.

26. The device of claim 24, wherein the liquid crystal layer is homogeneous.

27. The device of claim 24, wherein the device is capable of being implanted into the eye of a wearer.

28. The device of claim 24 wherein, when the device worn by a wearer, the substrate is fixed in position relative to the wearer's pupil.

29. The device of claim 24, wherein the liquid crystal layer is electrically addressable over an area of at least about 0.25 μm² without affecting the response of adjacent material.

30. The device of claim 29, further comprising a computerized controller capable of activating multiple segments of the liquid crystal layer.

31. The device of claim 30, wherein the controller is embedded into the ophthalmic device.

32. The device of claim 31, wherein the controller is configured to activate segments in a pattern corresponding to a mask that modulates the amplitude, the phase or both the amplitude and the phase of light is transmitted through the device into the eye of a user fitted with the device.

* * * * *